United States Patent
Negishi et al.

(12) 
(10) Patent No.: US 7,365,160 B2
(45) Date of Patent: Apr. 29, 2008

(54) MUTATED CONSTITUTIVELY ACTIVE NUCLEAR ORPHAN RECEPTOR

(75) Inventors: Masahiko Negishi, Chapel Hill, NC (US); Akiko Ueda, Durham, NC (US); Lars C. Pedersen, Chapel Hill, NC (US); Satoru Kakizaki, Durham, NC (US); Tatsuya Sueyoshi, Chapel Hill, NC (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 331 days.

(21) Appl. No.: 10/505,183

(22) PCT Filed: Feb. 19, 2003

(86) PCT No.: PCT/US03/05163

§ 371 (c)(1),
(2), (4) Date: Aug. 18, 2004

(87) PCT Pub. No.: WO03/070915

PCT Pub. Date: Aug. 28, 2003

(65) Prior Publication Data

US 2005/0107590 A1    May 19, 2005

Related U.S. Application Data

(60) Provisional application No. 60/358,500, filed on Feb. 19, 2002.

(51) Int. Cl.
    C07K 1/00      (2006.01)
    C12P 21/06     (2006.01)
    C12N 5/00      (2006.01)
(52) U.S. Cl. .................... 530/350; 435/69.1; 435/325
(58) Field of Classification Search ..................... None
    See application file for complete search history.

(56) References Cited

U.S. PATENT DOCUMENTS

| | | | |
|---|---|---|---|
| 5,639,616 | A | 6/1997 | Liao et al. |
| 5,756,448 | A | 5/1998 | Moore et al. |
| 5,932,699 | A | 8/1999 | Moore et al. |
| 6,235,873 | B1 | 5/2001 | Bromberg et al. |

FOREIGN PATENT DOCUMENTS

WO    WO 98/33819    *  8/1998

OTHER PUBLICATIONS

Koritschoner et al. 2001. Cell Growth and Differentiation 12:563-572.*
Tomko et al. 1997. PNAS 94:3352-3356.*
Tzammell et al. 2000. Mol. Cell Biol. 20:2951-2958.*
Wells, 1990, Biochemistry 29:8509-8517.*
Ngo et al., 1994, The Protein Folding Problem and Tertiary Structure Prediction, Merz et al., eds, Birkhauser, Boston, pp. 491-495.*
Baes et al., "A New Orphan Member of the Nuclear Hormone Receptor Superfamily that Interacts with a Subset of Retinoic Acid Response Elements," *Mol. Cell. Biol.* 14:1544-1552 (1994).
Choi et al., "Differential Transactivation by Two Isoforms of the Orphan Nuclear Hormone Receptor CAR," *J. Biol. Chem.* 272:23565-23571 (1997).
Kawamoto et al., "Estrogen Activation of the Nuclear Orphan Receptor CAR (Constitutive Active Receptor) in Induction of the Mouse *Cyp2b10* Gene," *Mol. Endocrinol.* 14:1897-1905 (2000).
Sueyoshi et al., "The Repressed Nuclear Receptor CAR Responds to Phenobarbital in Activating the Human *CYP2B6* Gene," *J. Biol. Chem.* 274:6043-6046 (1999).
Ueda et al., "Diverse Roles of the Nuclear Orphan Receptor CAR in Regulating Hepatic Genes in Response to Phenobarbital," *Mol. Pharmacol.* 61:1-6 (2002).
Ueda et al., "Residue Threonine 350 Confers Steroid Hormone Responsiveness to the Mouse Nuclear Orphan Receptor CAR," *Mol. Pharmacol.* 61:1284-1288 (2002).
Zelko and Negishi, "Phenobarbital-Elicited Activation of Nuclear Receptor CAR in Induction of Cytochrome P450 Genes," *Biochem. Biophys. Res. Commun.* 277:1-6 (2000).
Kirby et al., "Mutations in the DG Loop of Adenovirus Type 5 Fiber Knob Protein Abolish High-Affinity Binding to Its Cellular Receptor CAR," *J. Virol.* 73:9508-9514 (1999).
Roelvink et al., "Identification of a Conserved Receptor-Binding Site on the Fiber Proteins of CAR-Recognizing Adenoviridae," *Science* 286:1568-1571 (1999).
GenBank Accession No. Z30425, deposited on Mar. 8, 1994.

* cited by examiner

*Primary Examiner*—Manjunath Rao
*Assistant Examiner*—Shulamith H Shafer
(74) *Attorney, Agent, or Firm*—Klarquist Sparkman, LLP

(57) ABSTRACT

Disclosed are constitutively active nuclear orphan receptors (CAR), which include one or more mutations which decrease the constitutive nature of CAR in vitro. The resulting non-constitutively active nuclear orphan receptors can be used to screen for agents that metabolize xenochemicals and/or steroids.

13 Claims, 2 Drawing Sheets

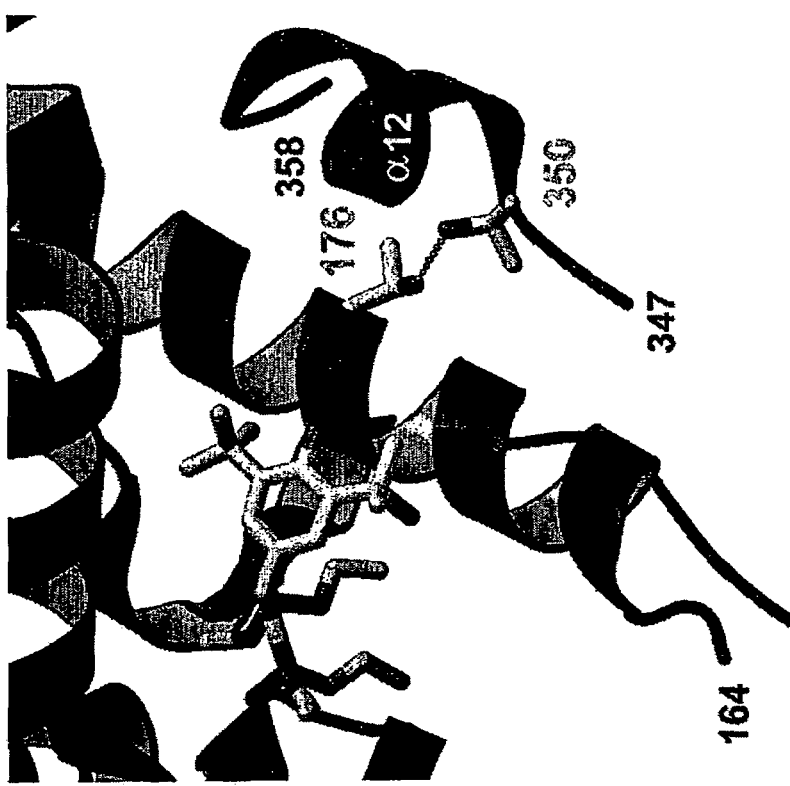
FIG. 2A. Entire CAR model
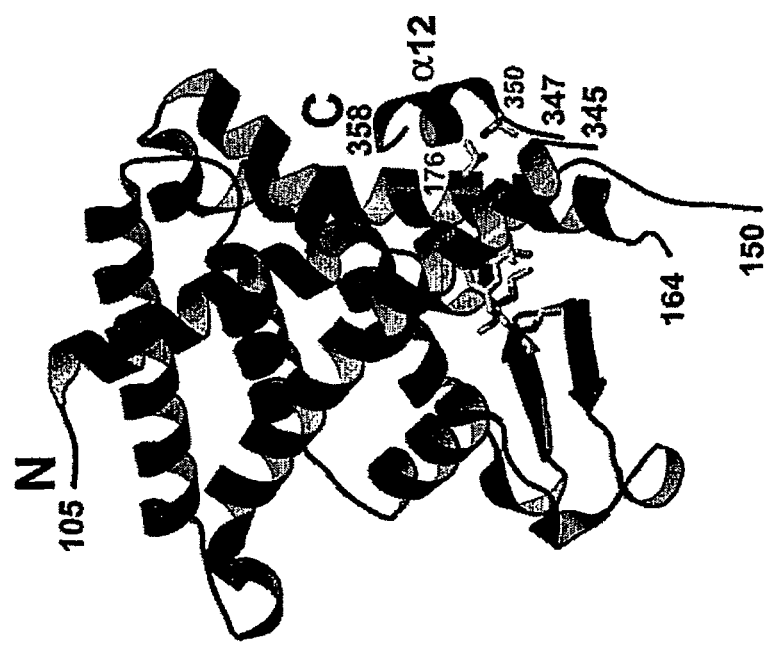
FIG. 2B. Model of hydrogen bond between T176 and T350

MUTATED CONSTITUTIVELY ACTIVE NUCLEAR ORPHAN RECEPTOR

CROSS-REFERENCE TO RELATED APPLICATION

This is the U.S. National Stage of International Application No. PCT/US2003/05163, filed Feb. 19, 2003 (published in English under PCT Article 21(2)), which in turn claims priority to U.S. Provisional Application No. 60/358,500 filed Feb. 19, 2002, herein incorporated by reference in its entirety.

FIELD

This disclosure relates to a constitutive active nuclear orphan receptor (CAR) which includes one or more mutations that render the peptide non-constitutively active, and methods of using the non-constitutive receptor (non-CAR).

BACKGROUND

The nuclear orphan receptor CAR (constitutively active receptor or constitutive androstane receptor) activates transcription of genes encoding various drug-metabolizing enzymes. For example, CAR activates xenochemical/steroid-metabolizing enzymes, in response to phenobarbital (PB) and other PB-type inducers (Sueyoshi and Negishi, Annu Rev Pharmacol Toxicol 41:123-43, 2001; Wei et al., Nature 407:920-3, 2000; Zelko and Negishi, Biochem Biophys Res Commun 277:1-6, 2000; and Ueda et al., Mol Pharmacol 61:1-6, 2002). Induction of these enzymes confers on organisms a higher metabolic capability to defend themselves against xenochemical toxicity and/or carcinogenicity.

In addition to xenochemicals such as PB and TCPOBOP (1,4-bis [2-(3,5-dichloropyridyloxy)]benzene), steroid hormones can modulate the CAR-mediated activation of gene transcription. Estrogens activate mouse CAR (mCAR) and induce the Cyp2b10 gene in mouse liver, whereas androgens and progesterone repress estrogen-activated mCAR (Kawamoto et al., Mol Endocrinol 14:1897-1905, 2000). However, unlike mCAR, human CAR (hCAR) does not respond to steroid hormones (Id.).

Direct activation of CAR in response to various drugs has been observed in vivo. CAR is retained in the cytoplasm of non-induced mouse livers and accumulates in the nucleus following PB treatment (Kawamoto et al., Mol Cell Biol 19:6318-22, 1999). However, in vitro, CAR is active even in the absence of agonistic chemicals in a cell-based transfection assay (Kawamoto et al., Mol Endocrinol 14:1897-1905, 2000). This constitutive activity makes it difficult to use CAR in vitro to screen for drugs that can enhance activation of xenochemical/steroid metabolizing enzymes. As a result, there have been attempts to alter CAR's in vitro constitutive activity.

Some steroid metabolites, such as androstenol, repress the constitutive activity of CAR in a cell-based transfection assay (Forman et al., Nature 395:612-5, 1998). In addition, PB and PB-type inducers can re-activate the repressed CAR in vitro (Sueyoshi et al., J Biol Chem 274:6043-6, 1999). Additional repressors such as progesterone, androgens, and CaMK inhibitor KN-62, as well as activators, such as estrogens, have been identified (Kawamoto et al., Mol Endocrinol 14:1897-1905, 2000). Thus, the re-activation is one method that can be used to regulate CAR in xenochemical-responsive fashion, at least, in vitro. However, whether this is also the regulatory mechanism in liver in vivo remains unclear.

It would be beneficial if the constitutively active nature of CAR could be converted into a xenochemical-responsive one, so that screening for drugs that can enhance activation of xenochemical/steroid metabolizing enzymes could also be readily performed in vitro, instead of only in vivo.

SUMMARY

Disclosed herein are polypeptides encoding a nuclear orphan receptor having decreased constitutive activity in vitro (referred to herein as non-CAR) as compared to the constitutive activity of a CAR, as well as isolated nucleic acids that encode such polypeptides. The disclosed non-CAR sequences can be used to identify agents, using an in vitro assay, that enhance activation of steroid and/or xenochemical metabolizing enzymes. Such agents can be administered to a subject exposed to one or more xenochemicals, or to a subject in whom increased levels of one or more steroids is desired, wherein the xenochemical and steroid are normally inducible by CAR. The disclosed non-CAR sequences can be used to analyze a sample, for example a sample suspected of including one or more CAR-responsive estrogen or estrogen-like chemicals, and/or one or more xenochemicals (such as phenobarbital).

For example, the non-CAR polypeptide includes one or more mutations, such as two or more mutations, corresponding to murine CAR (mCAR) position Thr176, mCAR position Leu352, mCAR position Leu353, mCAR position Glu355, human CAR (hCAR) hCAR position Leu342, and/or hCAR position Leu343. In a particular example, the non-CAR polypeptide includes a mutation corresponding to hCAR position Leu342 and/or Leu343. The disclosed mutation(s) render the CAR polypeptide less constitutively active, but do not interfere with the ability of the polypeptide to confer xenochemical metabolizing activity to a xenochemical-metabolizing enzyme, or steroid metabolizing activity to a steroid-metabolizing enzyme, wherein the xenochemical and steroid are normally inducible by CAR. Also disclosed are compositions including the disclosed polypeptides and nucleic acids. In one example, the composition includes a pharmaceutically acceptable carrier.

Kits including the disclosed polypeptide and nucleic acids are also disclosed, as are specific binding agents that distinguish between non-CAR and CAR polypeptides.

Also disclosed are methods of rendering a non-CAR peptide less constitutively active, while retaining the ability of CAR to induce a xenochemical metabolizing activity in response to a xenochemical, or to induce a steroid metabolizing activity in response to a steroid, wherein the xenochemical and steroid are normally inducible by CAR. The method includes introducing one or more mutations into a native CAR sequence, which substantially reduces the constitutive activity of CAR, but retains the ability to induce a xenochemical metabolizing activity in response to a xenochemical, or to induce a steroid metabolizing activity in response to a steroid, wherein the xenochemical and steroid are normally inducible by CAR.

Methods are disclosed for using the disclosed non-CAR polypeptides to screen one or more test agents, such as two or more test agents, to identify agents that activate steroid and/or xenochemical metabolizing enzymes, for example enhance such activation. The method includes exposing non-CAR to one or more test agents, and subsequently detecting steroid and/or xenochemical metabolizing activity.

For example, a cell expressing one or more non-CAR peptides is contacted with a test agent(s), and the resulting effect on steroid and/or xenochemical metabolizing activity determined. In one example, the cell contacted with the test agent(s) expresses one or more non-CAR peptides and a nucleic acid sequence (such as a reporter gene sequence) operably linked to an enhancer element If the agent(s) induces steroid and/or xenochemical metabolizing enzymes, non-CAR will be activated and interact with the enhancer element, thereby increasing transcription of the nucleic acid sequence operably linked to the enhancer element. The transcription of the nucleic acid sequence can be detected, for example the nucleic acid sequence can produce a detectable product, such as luciferase. The agents identified using this method can be administered to a subject exposed to one or more xenochemicals, for example to reduce the presence of xenochemcial in the subject. In addition, the agents identified using this method can be administered to a subject in whom altered levels of one or more steroids are desired. In one example, the agent is administered at a therapeutically effective dose to modulate steroid and/or xenochemical metabolizing enzyme activity.

Methods are disclosed for using the disclosed non-CAR sequences to analyze a sample, for example a sample suspected of including one or more CAR-responsive estrogen or estrogen-like chemicals, and/or one or more CAR-responsive xenochemicals (such as phenobarbital, PB). For example, a cell expressing one or more non-CAR peptides is contacted with the sample of interest, and the resulting effect on steroid and/or xenochemical metabolizing activity determined. In one example, the cell contacted with the sample expresses one or more non-CAR peptides and a nucleic acid sequence (such as a reporter gene sequence) operably linked to an enhancer element. If the sample contains agents that induce steroid and/or xenochemical metabolizing enzymes, non-CAR will be activated and interact with the enhancer element, thereby increasing transcription of the nucleic acid sequence operably linked to the enhancer element The transcription of the nucleic acid sequence can be detected, for example the nucleic acid sequence can produce a detectable product, such as luciferase. The presence of the detectable product indicates that the sample contains one or more CAR-responsive steroids and/or xenochemicals, such as estrogen or PB.

The foregoing and other objects, features, and advantages of the polypeptides, nucleic acids, agents and methods described herein will become more apparent from the following detailed description of several embodiments, which proceeds with reference to the accompanying figures.

BRIEF DESCRIPTION OF THE FIGURES

FIGS. 2A and 2B are ribbon diagrams showing the predicted mCAR three-dimensional structure, and the side-chain interaction between Thr350 and Thr176.

SEQUENCE LISTING

Figure 1:
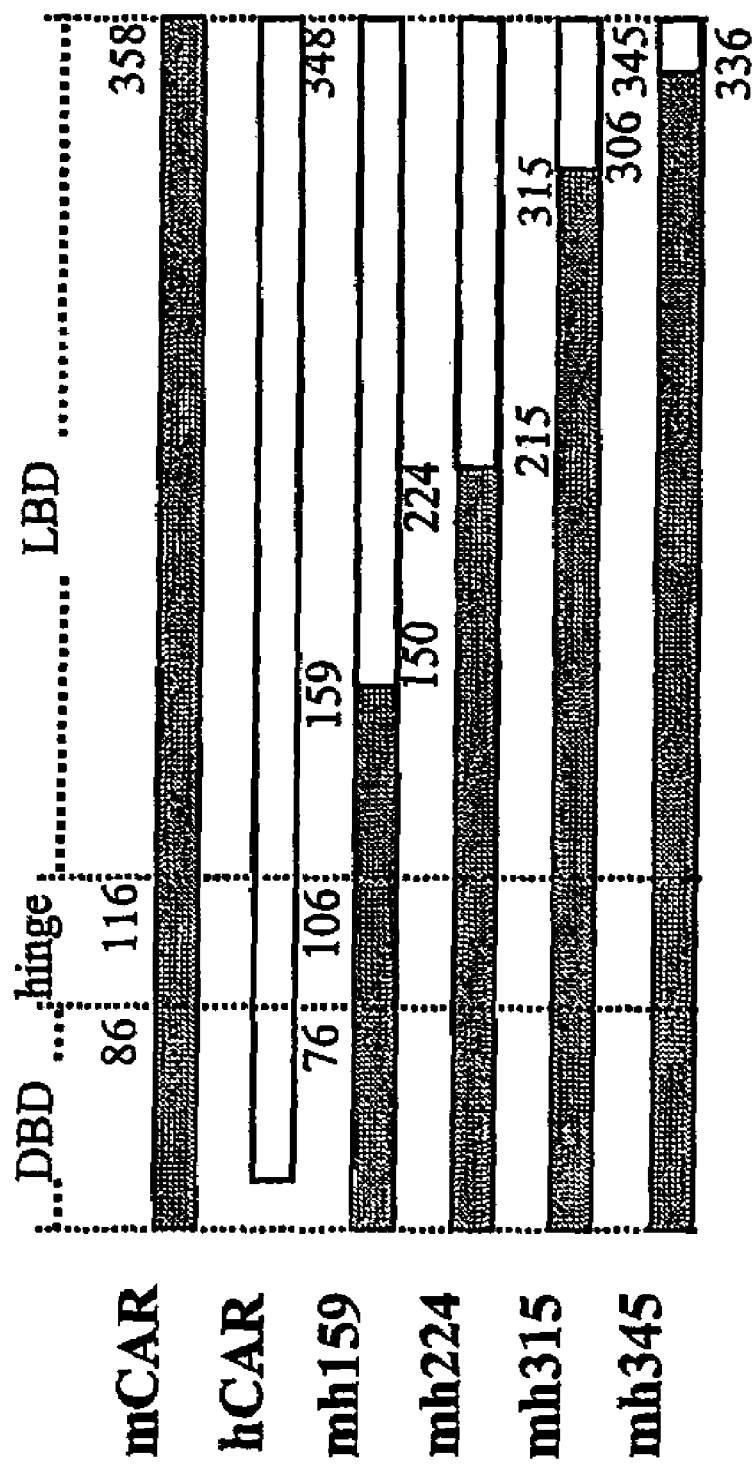
FIG. 1 is a schematic diagram showing putative domains of CAR proteins. Numbers indicate positions of amino acid residues at which chimeric receptors were constructed.

The nucleic acid sequences in the accompanying sequence listing are shown using standard letter abbreviations for nucleotides. Only one strand of each nucleic acid sequence is shown, but the complementary strand is understood as included by any reference to the displayed strand.

SEQ ID NOS: 1-14 are nucleic acid sequences showing primers used to introduce site-specific mutations into CAR.

SEQ ID NOS: 15 and 16 are the nucleotide and amino acid sequences, respectively, of murine CAR, GenBank Accession No. AF009327.

SEQ ID NOS: 17 and 18 are the nucleotide and amino acid sequences, respectively, of human CAR, GenBank Accession No. Z30425.

DETAILED DESCRIPTION OF SEVERAL EMBODIMENTS

Abbreviations and Terms

The following explanations of terms and methods are provided to better describe the present disclosure and to guide those of ordinary skill in the art in the practice of the present disclosure. As used herein, the singular forms "a" or "an" or "the" include plural references unless the context clearly dictates otherwise. For example, reference to "a protein" includes one or a plurality of such proteins, and reference to "the cell" includes reference to one or more cells and equivalents thereof known to those skilled in the art, and so forth.

Unless explained otherwise, all technical and scientific terms used herein have the same meaning as commonly understood to one of ordinary skill in the art to which this disclosure belongs.

Agent: Any substance, including, but not limited to, an antibody, chemical compound, molecule, nucleic acid, peptidomimetic, or protein.

Antibody: A molecule including an antigen binding site that specifically binds (immunoreacts with) an antigen. Examples include, but are not limited to, polyclonal antibodies, monoclonal antibodies, humanized monoclonal antibodies, and immunologically effective portions thereof.

Naturally occurring antibodies (e.g., IgG) include four polypeptide chains, two heavy (H) chains and two light (L) chains inter-connected by disulfide bonds. However, the antigen-binding function of an antibody can be performed by fragments of a naturally occurring antibody. Immunologically effective portions of monoclonal antibodies include, but are not limited to: Fab, Fab', F(ab')$_2$, Fabc and Fv portions (for a review, see Better and Horowitz, *Methods. Enzymol.* 178:476-96, 1989). Other examples of antigen-binding fragments include, but are not limited to: (i) an Fab fragment consisting of the VL, VH, CL and CH1 domains; (ii) an Fd fragment consisting of the VH and CH1 domains; (iii) an Fv fragment consisting of the VL and VH domains of a single arm of an antibody, (iv) a dAb fragment that consists of a VH domain; (v) an isolated complimentarily determining region (CDR); and (vi) an F(ab')$_2$ fragment, a bivalent fragment comprising two Fab fragments linked by a disulfide bridge at the hinge region. Furthermore, although the two domains of the Fv fragment are coded for by separate genes, a synthetic linker can be made that enables them to be made as a single protein chain (known as single chain Fv (scFv) by recombinant methods. Such single chain antibodies are also included.

"Specifically binds" refers to the ability of a "specific binding agent" to specifically react with a particular analyte, for example to specifically immunoreact with an antibody, or to specifically bind to a particular peptide sequence. The binding is a non-random binding reaction, for example between an antibody and an antigenic determinant. Binding specificity of an antibody is typically determined from the reference point of the ability of the antibody to differentially bind the specific antigen and an unrelated antigen, and therefore distinguish between two different antigens, particularly where the two antigens have unique epitopes. An antibody that specifically binds to a particular epitope is referred to as a "specific antibody."

Monoclonal or polyclonal antibodies can be produced to the disclosed non-CAR polypeptides, or fragments, fusions, or variants thereof. Optimally, antibodies raised against one or more epitopes on a non-CAR polypeptide antigen will specifically detect that polypeptide, and not a nuclear orphan receptor CAR polypeptide or other polypeptides. The determination that an antibody specifically binds to a particular polypeptide is made by any one of a number of standard immunoassay methods; for instance, Western blotting (See, e.g., Sambrook et al. (ed.), Molecular Cloning: A Laboratory Manual, 2nd ed., vol. 1-3, Cold Spring Harbor Laboratory Press, Cold Spring Harbor, N.Y., 1989).

To determine that an antibody preparation (such as a preparation produced in a mouse against a non-CAR polypeptide) specifically detects the appropriate polypeptide (e.g., a non-CAR polypeptide) by Western blotting, total cellular protein is extracted from cells and separated by SDS-polyacrylamide gel electrophoresis. The separated total cellular protein is transferred to a membrane (e.g., nitrocellulose), and the antibody preparation incubated with the membrane. After washing the membrane to remove non-specifically bound antibodies, the presence of specifically bound antibodies can be detected using an appropriate secondary antibody (e.g., an anti-mouse antibody) conjugated to an enzyme such as alkaline phosphatase since application of 5-bromo-4-chloro-3-indolyl phosphate/nitro blue tetrazolium results in the production of a densely blue-colored compound by immuno-localized alkaline phosphatase.

Substantially pure polypeptides suitable for use as an immunogen can be obtained from transfected cells, transformed cells, or wild-type cells. Polypeptide concentrations in the final preparation can be adjusted, for example, by concentration on an Amicon filter device, to the level of a few µg/ml. In addition, polypeptides ranging in size from full-length polypeptides to polypeptides having as few as nine amino acid residues can be utilized as immunogens. Such polypeptides can be produced in cell culture, can be chemically synthesized using standard methods, or can be obtained by cleaving large polypeptides into smaller polypeptides that can be purified. Polypeptides having as few as nine amino acid residues in length can be immunogenic when presented to an immune system in the context of a Major Histocompatibility Complex (MHC) molecule such as an MHC class I or MHC class II molecule. Accordingly, polypeptides having at least 9, 10, 11, 12, 13, 14, 15, 20, 25, 30, 35, 40, 45, 50, 55, 60, 70, 80, 90, 100, 150, 200, 250, 300, 350, 358 or more consecutive amino acid residues of a non-CAR polypeptide can be used as immunogens for producing antibodies.

Monoclonal antibodies to any of the polypeptides disclosed herein can be prepared from murine hybridomas according to the classic method of Kohler & Milstein (*Nature* 256:495, 1975) or a derivative method thereof. Polyclonal antiserum containing antibodies to the heterogeneous epitopes of any polypeptide disclosed herein can be prepared by immunizing suitable animals with the polypeptide (or fragment, fusion, or variant thereof), which can be unmodified or modified to enhance immunogenicity. An effective immunization protocol for rabbits can be found in Vaitukaitis et al. (*J. Clin. Endocrinol. Metab.* 33:988-91, 1971).

Antibody fragments can be used in place of whole antibodies and can be readily expressed in prokaryotic host cells. Methods of making and using immunologically effective portions of monoclonal antibodies, also referred to as "antibody fragments," are well known and include those described in Better & Horowitz (*Methods Ezymol.* 178:476-96, 1989), Glockshuber et al. (*Biochemistry* 29:1362-7, 1990), U.S. Pat. No. 5,648,237 ("Expression of Functional Antibody Fragments"), U.S. Pat. No. 4,946,778 ("Single Polypeptide Chain Binding Molecules"), U.S. Pat. No. 5,455,030 ("Immunotherapy Using Single Chain Polypeptide Binding Molecules"), and references cited therein.

CAR (nuclear orphan constitutive active receptor): The term "CAR" includes any CAR gene, cDNA, RNA, or protein from any organism, that has the property of being constitutively active in vitro and/or the ability in vivo to be inducible by a CAR-responsive steroid, such as estrogen, and/or the ability in vivo to be inducible by a CAR-responsive xenochemical, such as phenobarbital (PB) and TCPOBP. For example, CAR can induce a PB enhancer element in the presence of the xenochemical PB, by increasing transcription of a sequence operably linked to the PB enhancer element.

In one example, CAR includes mammalian CAR sequences, such as mouse CAR (mCAR, for example Genbank Accession Nos. AF009327 and AAC53349) and human CAR (hCAR, for example Genbank Accession Nos. U90716 and AAC51234). In another example, a CAR sequence includes a full-length wild-type (or native) sequence, as well as CAR allelic variants, variants, fragments, homologs or fusion sequences that retain the ability to be constitutively active in vitro and/or the ability to activate a PB enhancer element in the presence of PB in vivo. In certain examples, CAR will have at least 80% sequence identity, for example 85%, 90%, 95%, or 98% sequence identity to a native CAR.

CAR transcription factor sequences, when expressed in a cell, activate enhancer elements of genes that encode various drug-metabolizing enzymes, such as xenochemical/steroid-metabolizing enzymes. For example, in response to PB, CAR can activate a PB enhancer element such as NR1, which increases transcription of sequences operably linked to the enhancer element. Although such activation occurs in response to a CAR-responsive xenochemical or steroid, in vitro this activation can occur non-specifically, that is, in the absence of a xenochemical or steroid. Activation and the responsiveness of CAR can be measured using the cell-based transfection assay described in EXAMPLE 1.

Non-CAR: A less constitutively active CAR that retains the ability to be induced by CAR-responsive xenochemicals and steroids. For example, includes any nuclear orphan receptor constitutively active receptor (or constitutive androstane receptor), that is not substantially constitutively active in vitro, such that the receptor has sufficiently low activity that its induction by a CAR-responsive steroid and/or xenochemical can be detected in vitro when performing a cell-based transfection assay as described in EXAMPLE 1. In particular non-limiting examples, non-CAR has about 50% or less, 25% or less, 10% or less, 5% or less or 2% or less or even 0% constitutive activity as compared to CAR for example in an in vitro cell-based transfection assay.

Examples of non-CAR sequences include, but are not limited to, CAR sequences having one or more mutations corresponding to mCAR position Thr176 and/or hCAR position Leu 342. Such mutations render the non-CAR polypeptide substantially non-constitutively active in vitro. In a particular example, non-CAR can be activated by agonistic compounds, such as CAR-responsive xenochemicals and/or steroids. Activation and the responsiveness of non-CAR can be measured using the cell-based transfection assay described in EXAMPLE 1.

cDNA (complementary DNA): A piece of DNA lacking internal, non-coding segments (introns) and regulatory sequences that determine transcription. cDNA can be synthesized by reverse transcription from messenger RNA extracted from cells.

Comprises: A term that means "including." For example, "comprising A or B" means including A or B, or both A and B, unless clearly indicated otherwise.

Conservative substitution: A substitution of one amino acid residue in a protein sequence for a different amino acid residue having similar biochemical properties. Typically, conservative substitutions have little to no impact on the activity of a resulting polypeptide. For example, ideally, a non-CAR peptide including one or more conservative substitutions (for example no more than 2, 5 or 10 substitutions) retains non-CAR activity, such as being substantially constitutively active in vitro, and the ability to be induced by CAR-responsive xenochemicals and steroids. A polypeptide can be produced to contain one or more conservative substitutions by manipulating the nucleotide sequence that encodes that polypeptide using, for example, standard procedures such as site-directed mutagenesis or PCR. In one example, such variants can be readily selected for additional testing by performing a cell-based transfection assay (such as those described in EXAMPLES 1-7) to determine if the variant retains non-CAR activity.

Examples of amino acids that can be substituted for an original amino acid in a protein and are regarded as conservative substitutions include: Ser for Ala; Lys for Arg; Gln or His for Asn; Glu for Asp; Ser for Cys; Asn for Gln; Asp for Glu; Pro for Gly; Asn or Gln for His; Leu or Val for Ile; Ile or Val for Leu; Arg or Gln for Lys; Leu or Ile for Met; Met, Leu or Tyr for Phe; Thr for Ser; Ser for Thr; Tyr for Trp; Trp or Phe for Tyr; and Ile or Leu for Val. Further information about conservative substitutions can be found, for example in: Ben-Bassat et al., (*J. Bacteriol.* 169:751-7, 1987), O'Regan et al., (*Gene* 77:237-51, 1989), Sahin-Toth et al., (*Protein Sci.* 3:240-7, 1994), Hochuli et al., (*Bio/Technology* 6:1321-5, 1988) and in standard textbooks of genetics and molecular biology.

Corresponding: A particular nucleic acid or amino acid in one sequence is said to correspond to a nucleic acid or amino acid in another sequence, if when the sequences are optimally aligned (for example using the software lalign or BLAST) the nucleic acids or amino acids align with one another. For example the following sequence: KMEDAV, amino acids 235-240 of mCAR, is said to "correspond" to the sequence TIEDGA, amino acids 225-230 of hCAR (see FIG. 1 Choi et al. *J. Biol. Chem.* 272:23565-71, 1997, for a fill alignment of mCAR and hCAR). Therefore, K235 of mCAR corresponds to T225 of hCAR. In addition T176 of mCAR corresponds to T166 of hCAR and T176 of rat CAR. L352 of mCAR corresponds to L342 of hCAR and L352 of rat CAR.

Deletion: The removal of a nucleic acid or amino acid sequence, for example DNA, the regions on either side being joined together.

DNA (Deoxyribonucleic acid): A long chain polymer that includes the genetic material of most living organisms (some viruses have genes including ribonucleic acid, RNA). The repeating units in DNA polymers are four different nucleotides, each of which includes one of the four bases, adenine, guanine, cytosine and thymine bound to a deoxyribose sugar to which a phosphate group is attached. Triplets of nucleotides, referred to as codons, in DNA molecules code for amino acid in a polypeptide. The term codon is also used for the corresponding (and complementary) sequences of three nucleotides in the mRNA into which the DNA sequence is transcribed.

Enhancer element: A sequence that regulates transcription of a nucleic acid sequence upon activation by an agent. For example, PB and PB-type compounds (such as chlorinated pesticides, polychlorinated biphenyls, and chlorpromazine) activate NR1 and PBREM enhancer elements, which results in increased transcription of sequences operably linked to these elements, such as a reporter gene sequence. For example, transcription can be increased by at least 10%, at least 20%, at least 50%, at least 75%, at least 100%, at least 200% or even greater, as compared to the level of transcription in the absence of the agent.

Specific examples include, but are not limited to the PB-responsive enhancer NR1 of the CYP2B gene (see Kawamoto et al. *Mol. Endocrinol.* 14:1897-1905, 2000); the PB-responsive enhancer PBREM of the Cy2b10 gene (see Sueyoshi et al *J. Biol. Chem.* 274:6043-6, 1999); the steroid/rifampicin-response element of the human CYP3A4 gene; and gtPBREM of the human UDP-glucuronosyltransferase gene (Sugatani et al., *Hepatology* 33, 1232-8, 2001).

Isolated: A biological component (such as a nucleic acid or protein) that has been substantially separated, produced apart from, or purified away from other biological components in the cell of the organism in which the component occurs, i.e., other chromosomal and extrachromosomal DNA and RNA, and proteins. Nucleic acids and proteins which have been isolated include nucleic acids and proteins purified by standard purification methods. The term also includes nucleic acids and proteins prepared by recombinant expression in a host cell as well as chemically synthesized nucleic acids, proteins and peptides.

Label: An agent that generates an amount of detectable signal. Examples of labels include, but are not limited to: fluorophores, chemiluminescent molecules, radioactive isotopes, ligands, and enzymes. Methods for labeling and guidance in the choice of labels appropriate for various purposes are discussed, e.g., in Sambrook et al., *Molecular Cloning. A Laboratory Manual*, Cold Spring Harbor Laboratory Press (1989) and Ausubel et al., *Current Protocols in Molecular Biology*, Greene Publishing Associates and Wiley-Intersciences (1987).

Mammal: Includes both human and non-human mammals. Examples of mammals include, but are not limited to: primates (such as apes and chimpanzees), dogs, cats, rats, mice, cows, pigs, sheep, horses, goats, and rabbits.

Mutation: A substitution of a nucleic acid in a DNA sequence for a different nucleic acid, or a substitution of an amino acid residue in a protein sequence for a different amino acid residue. Mutations of a DNA or protein sequence can result in a different phenotype than the wild-type sequence. For example, a protein having one or more mutations, such as two or more mutations, can have a different activity than the corresponding non-mutated (or wild-type) protein.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

ORF (open reading frame): A series of nucleotide triplets (codons) coding for amino acids without any termination codons. These sequences are usually translatable into a peptide.

Pharmaceutically acceptable carriers: The pharmaceutically acceptable carriers useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of the peptides, nucleic acids, and other agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

PCR (polymerase chain reaction): A technique in which cycles of denaturation, annealing with primer, and then extension with DNA polymerase are used to amplify the number of copies of a target DNA sequence.

Polynucleotide: A linear nucleic acid sequence of any length. Therefore, a polynucleotide includes molecules that are at least 15, 25, 50, 75, 100, 200, 300, or 400 (oligonucleotides) and also nucleotides as long as a full-length cDNA.

Promoter: An array of nucleic acid control sequences that direct transcription of a nucleic acid. A promoter includes necessary nucleic acid sequences near the start site of transcription, such as, in the case of a polymerase II type promoter, a TATA element. A promoter also optionally includes distal enhancer or repressor elements that can be located as much as several thousand base pairs from the start site of transcription.

Purified: The term purified does not require absolute purity; rather, it is intended as a relative term. Thus, for example, a purified peptide preparation is one in which the peptide or protein is more enriched than the peptide or protein is in its environment within a cell, such that the peptide is substantially separated from cellular components (nucleic acids, lipids, carbohydrates, and other polypeptides) that may accompany it. In another example, a purified peptide preparation is one in which the peptide is substantially-free from contaminants, such as those that might be present following chemical synthesis of the peptide. In particular examples, a substantially purified protein or peptide refers to proteins or peptides that are at least 50% pure, for example at least 70% pure.

Examples of methods that can be used to purify an protein, include, but are not limited to the methods disclosed in Sambrook et al (*Molecular Cloning. A Laboratory Manual*, Cold Spring Harbor, N.Y., 1989, Ch. 17). Protein purity can be determined by for example, polyacrylamide gel electrophoresis of a protein sample, followed by visualization of a single polypeptide band upon staining the polyacrylamide gel; high-pressure liquid chromatography; sequencing; or other conventional methods.

Reporter gene: A DNA sequence whose expression can be assayed, for example by detecting the production of a product. Examples include, but are not limited to lacz, β-galactosidase, amino acid biosynthetic genes such as the yeast LEU2 gene, luciferase or the mammalian chloramphenicol transacetylase (CAT) gene. Reporter genes can be integrated into the chromosome of a cell or can be carried on autonomously replicating plasmids.

Recombinant: A nucleic acid sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

Sample: A material to be analyzed. For example, using the methods disclosed herein, a sample can be analyzed for the presence or absence of a CAR-responsive steroid and/or xenochemical.

In one example, a sample is a biological sample, and can contain genomic DNA, cDNA, RNA, or protein obtained from the cells of a subject Other examples of biological samples, include, but are not limited to: peripheral blood, serum, plasma, urine, cerebrospinal fluid, pleural fluid, synovial fluid, peritoneal fluid, gastric fluid, saliva, lymph fluid, interstitial fluid, sputum, stool, physiological secretions, tears, mucus, sweat, milk, semen, seminal fluid, vaginal secretions, fluid from ulcers and other surface eruptions, blisters, and abscesses, tissue biopsy, surgical specimen, fine needle aspriates, amniocentesis samples and autopsy material.

In another example, a sample is an environmental sample. An environmental sample includes samples obtained from extreme environments including, for example, hot sulfur pools, volcanic vents, and frozen tundra. Other types of environmental samples include, but are not limited to: in horticulture and agricultural testing the sample can be a plant, fertilizer, soil, liquid or other horticultural or agricultural product; in food testing the sample can be fresh food or processed food, and in environmental testing the sample can be liquid, soil, sewage treatment, sludge and any other sample in the environment which is considered or suspected of containing one or more CAR-responsive steroids and/or xenochemicals.

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods. This homology is more significant when the orthologous proteins or cDNAs are derived from species that are more closely related (e.g., human and mouse sequences), compared to species more distantly related (e.g., human and *C. elegans* sequences).

Methods of alignment of sequences for comparison are well known. Various programs and alignment algorithms are described in: Smith & Waterman, *Adv. Appl. Math.* 2:482, 1981; Needleman & Wunsch, *J. Mol. Biol.* 48:443, 1970;

Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site.

For comparisons of amino acid sequences of greater than about 30 amino acids, the Blast 2 sequences function is employed using the default BLOSUM62 matrix set to default parameters, (gap existence cost of 11, and a per residue gap cost of 1). Non-CAR homologs are typically characterized by possession of at least 70% sequence identity counted over the full-length alignment with a non-CAR amino acid sequence using the NCBI Basic Blast 2.0, gapped blastp with databases such as the nr or swissprot database. Queries searched with the blastn program are filtered with DUST (Hancock and Armstrong, 1994, *Comput. App. Biosci.* 10:67-70). Other programs use SEG. In addition, a manual alignment can be performed. Proteins with even greater similarity to non-CAR sequences (which can be used in the disclosed methods) will show increasing percentage identities when assessed by this method, such as at least 75%, 80%, 85%, 90%, 95%, or 99% sequence identity.

When aligning short peptides (fewer than around 30 amino acids), the alignment should be performed using the Blast 2 sequences function, employing the PAM30 matrix set to default parameters (open gap 9, extension gap 1 penalties). Non-CAR proteins with even greater similarity to the reference sequence (which can be used in the disclosed methods) show increasing percentage identities when assessed by this method, such as at least 80%, 85%, 90%, 95%, 98%, or 99% sequence identity. When less than the entire sequence is being compared for sequence identity, homologs will typically possess at least 75% sequence identity over short windows of 10-20 amino acids, and can possess sequence identities of at least 85%, 90%, 95% or 98% depending on their identity to the reference sequence. Methods for determining sequence identity over such short windows are described at the NCBI web site.

One indication that two nucleic acid molecules are closely related is that the two molecules hybridize to each other under stringent conditions. Stringent conditions are sequence-dependent and are different under different environmental parameters. Nucleic acid molecules that hybridize under stringent conditions to a non-CAR gene sequence (which can be used in the disclosed methods) typically hybridize to a probe based on either an entire non-CAR gene or selected portions of the gene, respectively, under conditions described in EXAMPLE 9. An alternative (and not necessarily cumulative) indication that two nucleic acid sequences are substantially identical is that the polypeptide which the first nucleic acid encodes is immunologically cross reactive with the polypeptide encoded b the second nucleic acid.

Nucleic acid sequences that do not show a high degree of identity to a non-CAR sequence may nevertheless encode identical or similar (conserved) amino acid sequences, due to the degeneracy of the genetic code. Changes in a non-CAR nucleic acid sequence can be made using this degeneracy to produce multiple nucleic acid molecules that all encode substantially the same protein, and can be used in the disclosed methods. Such homologous nucleic acid sequences can, for example, possess at least 70%, 80%, 90%, 95%, 98%, or 99% sequence identity determined by this method.

One of skill in the art will appreciate that these sequence identity ranges are provided for guidance only; it is possible that strongly significant non-CAR homologs can be obtained that fall outside the ranges provided.

Specific binding agent: An agent that binds substantially only to a defined target. For example, a non-CAR binding agent includes non-CAR antibodies, such as polyclonal or monoclonal antibodies, and other agents (such as peptides or drugs) that bind substantially to only a non-CAR protein, and ideally do not bind to a CAR protein.

Steroid: A group name for lipids that contain a hydrogenated cyclopentanoperhydrophenanthrene ring system. Examples include, but are not limited to: progesterone, androgens, testosterone, estradiol, estrogen, cardiac aglycones, bile acids, sterols (such as cholesterol), toad poisons, saponins and some of the carcinogenic hydrocarbons. In one example, a CAR-responsive steroid, such as estrogen, is one that can activate CAR and result in steroid metabolizing or degrading activity.

Steroid-metabolizing enzymes are enzymes that process and/or degrade steroids, thereby decreasing their toxicity and/or carcinogenicity. Such activity is referred to as steroid metabolizing or degrading activity. Without wishing to be bound to a particular theory, it is thought that in mice, in response to estrogen exposure, CAR in the cytoplasm translocates into the nucleus, forms a heterodimer with the appropriate receptor, and activates the appropriate enhancer element leading to increased expression of genes encoding for estrogen-metabolizing enzymes. In contrast, in mice, progesterone and androgens repress CAR activity.

Subject: Includes any mammalian subject, such as a human or veterinary subject.

Test agent: An agent to be tested for a desired activity, such as an ability to promote the metabolization of one or more CAR-responsive xenochemicals or one or more CAR-responsive steroids.

Transformed: A cell into which has been introduced a nucleic acid molecule by molecular biology techniques. As used herein, transformation encompasses all methods by which a nucleic acid molecule can be introduced into such a cell, including transfection with viral vectors, transformation with plasmid vectors, and introduction of naked DNA by electroporation, lipofection, and particle gun acceleration.

Variants, fragments or fusion proteins: The disclosed non-CAR sequences include variants, fragments, and fusions thereof that retain desired properties, such as responsiveness to desired test agents, such as CAR-responsive xenochemicals and estrogens and/or the ability to enhance transcription of xenochemical and/or steroid metabolizing enzymes. DNA sequences which encode a non-CAR protein or fusion thereof, or a fragment or variant of thereof (for example a fragment or variant having 80%, 90% or 95% sequence identity to a non-CAR sequence) can be engineered to allow the protein to be expressed in eukaryotic cells or organisms, bacteria, insects, and/or plants. To obtain expression, the DNA sequence can be altered and operably linked to other regulatory sequences. The final product, which contains the regulatory sequences and the protein, is referred to as a vector. This vector can be introduced into eukaryotic, bacteria, insect, and/or plant cells. Once inside the cell the vector allows the protein to be produced.

A fusion protein including a protein, such as non-CAR (or variants, polymorphisms, mutants, or fragments thereof) linked to other amino acid sequences that do not inhibit the desired activity of non-CAR, for example the characteristic of having decreased constitutive activity in vitro. In one example, the other amino acid sequences are no more than about 10, 20, 30, or 50 amino acid residues in length.

One of ordinary skill in the art will appreciate that the DNA can be altered in numerous ways without affecting the biological activity of the encoded protein. For example, PCR can be used to produce variations in the DNA sequence which encodes non-CAR. Such variants can be variants optimized for codon preference in a host cell used to express the protein, or other sequence changes that facilitate expression.

Vector: A nucleic acid molecule as introduced into a host cell, thereby producing a transformed host cell. A vector can include nucleic acid sequences that permit it to replicate in the host cell, such as an origin of replication. A vector can also include one or more selectable marker genes and other genetic elements.

Xenochemical: A chemical foreign to an organism (i.e., a non-endogenous chemical). Examples include, but are not limited to, a drug, pesticide, or environmental contaminant In one example, a CAR-responsive xenochemical is one that can activate CAR and result in xenochemical-metabolizing or degrading activity. Particular examples of CAR-responsive xenochemicals include, but are not not limited to: phenobarbital (PB); 1,4-bis [2-(3,5-dichloropyridyloxy)] benzene (TCPOBOP); and PB-type inducers such as chlorinated pesticides, methoxychlor, 1,1,1-trichloro-1,2-bis (o.p'-chlorophenyl)ethane); chlorpromazine; polychlorinated biphenyls; and organic solvents (i.e. acetone and pyridine).

Xenochemical-metabolizing enzymes, such as cytochrome P450s and specific transferases such as glutathione S-transferases, glucuronosyltransferases, and sulfotransferases, are enzymes that process and/or degrade xenochemicals, thereby decreasing their toxicity and/or carcinogenicity. Such activity is referred to as xenochemical metabolizing or degrading activity. Without wishing to be bound to a particular theory, it is thought that in response to xenochemical exposure, CAR in the cytoplasm translocates into the nucleus, forms a heterodimer with the appropriate receptor, and activates the appropriate enhancer element leading to increased expression of genes encoding for xenochemical-metabolizing enzymes.

Non-Constitutively Active Nuclear Orphan Receptors

The nuclear orphan receptor CAR displays strong constitutive activity in a cell-based transfection assay, whereas the activation is tightly regulated by various endogenous and exogenous agonistic chemicals in liver in vivo. Until now, the structural basis for the constitutive activity was unknown. To identify the structural basis for the constitutive active nature of CAR, site-directed mutagenesis was used to convert CAR from a constitutive active receptor to a xenochemical (agonist)-responsive receptor.

It is demonstrated herein that the hormone response activity of CAR resides near or within the AF-2 domain of mCAR, and that a single mutation of mCAR Thr350 to the corresponding Met in human CAR (hCAR) abolished the repressive activity of mCAR by steroid hormones. Thr350 appears to regulate the hormone responsiveness of mCAR by interfering indirectly with an interaction of the receptor with co-activator. Therefore, mutations in the amino acid corresponding to mCAR Thr350 (such as an Thr350Met mutation) can be used to decrease or eliminate hormone responsiveness of CAR. Using molecular modeling, it was determined that the side chains of mCAR Thr350 and mCAR Thr176 interact (see FIGS. 2A and 2B). Following a mutational analysis, it is herein demonstrated that residues Thr176 and Leu352 each confer constitutive activity to mCAR. In addition, it is herein demonstrated that hCAR Leu342, alone or in combination with hCAR Leu 343, confers constitutive activity to hCAR.

Polypeptides, such as purified polypeptides, that encode a non-constitutively active nuclear orphan receptor (non-CAR) are disclosed. In one example, the non-CAR polypeptides include one or position Leu352, mCAR position Leu353, mCAR position Glu355, hCAR position Leu342, and/or hCAR position Leu 343, that render the polypeptide substantially non-constitutively active, such as a decrease in constitutive activity of at least 20%, at least 50%, at least 75%, at least 80%, at least 90%, at least 95%, at least 98%, or even 100%. For example, in the absence of a CAR-responsive steroid and/or xenochemical (that is a xenochemical or steroid that would normally induce CAR), the receptor does not substantially confer the ability of an enhancer element to increase transcription of a sequence operably linked to the enhancer element. Constitutive activity can be measured using the cell based transfection assay described in EXAMPLE 1.

In one example, one or more mutations in hCAR render the polypeptide non-constitutively active, but does not substantially eliminate the ability of the polypeptide to confer xenochemical metabolizing activity to a xenochemical-metabolizing enzyme that would normally be induced by CAR. For example, in the presence of a CAR-responsive xenochemical, the xenochemical confers the ability of the non-CAR polypeptide to increase transcription of a nucleic acid sequence (such as a xenochemical metabolizing enzyme) operably linked to an enhancer element.

Examples of specific mutations that can be made to an mCAR polypeptide to render it substantially non-constitutively active include, but are not limited to: a Thr176 to Val176 (T176V) mutation, a Thr176 to Leu176 (T176L) mutation, a Leu352 to Ala352 (L352A) mutation, a Leu353 to Ala353 (l253A) and/or a Glu355 to Ala355. Examples of specific mutations that can be made to an hCAR polypeptide to render it substantially non-constitutively active include, but are not limited to: a Leu342 to Ala342 (L342A) mutation, a Leu343 to Ala343 (L343A) mutation, or both a L342A and a L343A mutation. One skilled in the art will understand that corresponding mutations can be made in other CAR peptides, such as Leu352 to Ala352 of rat CAR.

In a further example, a non-CAR polypeptide can also include one or more, such as two or more conservative amino acid substitutions, as long as the polypeptide retains non-CAR biological activity; that is, the substitutions do not substantially eliminate the non-constitutive activity of the polypeptide. In one example, the non-CAR polypeptide includes no more than about 10, such as no more than 5, or no more than 2, conservative amino acid substitutions.

In a particular example, a non-CAR polypeptide confers xenochemical metabolizing activity to a CAR-responsive xenochemical-metabolizing enzyme, wherein the xenochemical metabolizing activity can be detected in vitro.

In one example, expression of the xenochemical-metabolizing enzyme is regulated by an enhancer element. Xenochemical-metabolizing enzymes can metabolize and/or degrade xenochemicals, including, but not limited to phenobarbital (PB) or 1,4-bis [2-(3,5-dichloropyridyloxy)]benzene (TCPOBOP).

In an additional or alternative example, a non-CAR polypeptide confers steroid metabolizing activity to a steroid-metabolizing enzyme, wherein the steroid metabolizing activity can be detected in vitro. Steroid-metabolizing enzymes can metabolize and/or degrade steroids, including, but not limited to estrogen or estradiol.

Isolated nucleic acid molecules that encode the non-CAR polypeptides are disclosed. Such isolated nucleic acids can be operably linked to a promoter sequence. The nucleic acid can be a recombinant nucleic acid and/or part of a vector. Cells transformed with recombinant nucleic acids encoding a non-CAR polypeptide are disclosed. In one example, such cells include steroid metabolizing activity and/or xenochemical metabolizing activity. Transgenic mammals, such as a transgenic mouse, that include a recombinant nucleic acid encoding a non-CAR polypeptide are disclosed.

Specific-binding agents, such as drugs or antibodies, are disclosed that specifically bind to a non-CAR polypeptide but do not bind to a nuclear orphan receptor CAR. Also disclosed are compositions which include the disclosed peptides and/or nucleic acids. In one example, the composition includes a pharmaceutically acceptable carrier.

Kits are disclosed that include a non-CAR polypeptide and/or a non-CAR nucleic acid. Such kits can include one or more agents that increase transcription of a nucleic acid sequence operably linked to an enhancer element, as compared to transcription in the absence of the agent. Examples of agents that can be included in the kit, include but are not limited to one or more, such as two or more, CAR-responsive steroids and/or xenochemicals.

Methods of Using Non-Constitutively Active Nuclear Orphan Receptors

Methods are disclosed for generating a substantially non-constitutively active CAR. The method includes introducing one or more mutations, such as two or more mutations, such as no more than two mutations, into a native CAR sequence. Ideally, the mutation(s) that renders CAR non-constitutively active do not substantially interfere with the ability of non-CAR to be responsive to a CAR-responsive xenochemical or CAR-responsive steroid. That its, non-CAR molecules retain the ability to confer steroid metabolizing activity to a steroid-metabolizing enzyme and/or xenochemical metabolizing activity to a xenochemical-metabolizing enzyme.

Examples of mutations that render non-CAR non-constitutively active, include, but are not limited to one or more mutations corresponding to mCAR positions Thr176, Leu352, Leu353, as well as hCAR positions L343 and/or Leu342. Specific examples of mutations include, but are not limited to a T176V mutation, a T176L mutation, a L352A mutation, a L353A mutation, a L342A mutation, and/or a L343A mutation.

Also disclosed are methods for screening one or more test agents, such as two or more test agents, to identify agents that activate xenochemical and/or steroid metabolizing enzymes, for example enhance such activation. The method includes exposing non-CAR to a test agent(s), and subsequently detecting steroid and/or xenochemical metabolizing activity. The non-CAR polypeptide is substantially non-constitutively active, while retaining the ability to be substantially responsive to CAR-responsive test agents, xenochemicals, and steroids. For example, a cell expressing one or more non-CAR peptides is contacted with the test agent(s), and the resulting effect on steroid and/or xenochemical metabolizing activity determined. In one example, the cell contacted with the test agent(s) includes one or more non-CAR peptides and a nucleic acid sequence (such as a reporter gene sequence) operably linked to a xenochemical or steroid-specific enhancer element. If the agent(s) induces steroid and/or xenochemical metabolizing enzymes, non-CAR will be activated and interact with the enhancer element, thereby increasing transcription of the nucleic acid sequence operably linked to the enhancer element. Transcription of the nucleic acid sequence can be detected, for example by analyzing mRNA or cDNA expression. Alternatively, the nucleic acid sequence is a reporter gene sequence which produces a detectable product, such as luciferase or CAT. A determination can be made as to whether the test agent(s) increases transcription of the nucleic acid sequence operably linked to the enhancer element For example, presence of the product indicates that test agent conferred the ability of the non-CAR polypeptide to activate transcription of the nucleic acid sequence operably linked to the enhancer element thereby resulting in production of the product from the reporter gene. Such agents are good candidates for reducing the presence of a xenochemical, such as in a subject. In contrast, absence of detectable product indicates that the non-CAR polypeptide was not activated by the test agent, and thus the test agent does not increase transcription of a nucleic acid sequence operably linked to an enhancer element.

In one example, the cell is a transformed cell. In another example, the transformed cell is in a subject, such as a transgenic mammal, and the test agent is administered to the mammal. Examples of cells that can be used, include, but are not limited to a bacterial cell, yeast cell, plant cell, fungal cell, or mammalian cell, such as a liver cell.

Examples of enhancer elements that can be used to practice the methods disclosed herein include, but are not limited to a xenochemical or a steroid metabolizing enzyme enhancer element. An example of a xenochemical enhancer element is a PB enhancer element, such as NR1 or PBREM sequences.

In one example, downstream products of non-CAR can be detected as an alternative to detecting the presence of a product encoded by the nucleic acid sequence operably linked to the enhancer element. In this example, the cell expresses non-CAR. For example, a transgenic mammal, such as a transgenic mouse, expressing non-CAR, is administered one or more test agents.

The ability of the non-CAR polypeptide to increase transcription of one or more non-CAR regulated genes can be determined, for example by measuring cDNA expression of such regulated genes. Presence of induction or repression of a non-CAR regulated gene indicates that test agent conferred the ability of the non-CAR polypeptide to alter transcription of the non-CAR regulated gene. In contrast, absence of induction or repression of a non-CAR regulated gene indicates that the non-CAR polypeptide was not activated by the test agent, and thus the test agent does not alter transcription of the non-CAR regulated gene. Examples of non-CAR regulated genes include, but are not limited to, CYP2B10 and PB-induced enzymes.

The agents identified using this method which have the ability to induce xenochemical metabolizing activity can be administered to a subject exposed to one or more CAR-responsive xenochemicals, in order to reduce the presence of the xenochemical in the subject. The agents identified using this method which have the ability to induce steroid metabolizing activity can be administered to a subject in whom altered levels of CAR-responsive steroids is desired. In one example, the agent is administered at a therapeutically effective dose to increase steroid and/or xenochemical metabolizing enzyme activity.

Methods are disclosed for using the disclosed non-CAR sequences to analyze a sample, for example a sample suspected of including one or more CAR-responsive estrogen or estrogen-like chemicals, and/or one or more CAR-responsive xenochemicals (such as PB). For example, a cell expressing one or more non-CAR peptides, such as a transgenic cell, is contacted with the sample of interest, and the resulting effect on steroid and/or xenochemical metabolizing activity determined. For example, the cell contacted with the sample can express one or more non-CAR peptides and a nucleic acid sequence (such as a reporter gene sequence) operably linked to an enhancer element. If the sample contains an agent(s) that induces steroid and/or xenochemical metabolizing enzymes, non-CAR will be activated and interact with the enhancer element, thereby increasing transcription of the nucleic acid sequence operably linked to the enhancer element. The transcription of the nucleic acid sequence can be detected, for example the nucleic acid sequence can produce a detectable product, such as luciferase. The presence of the detectable product indicates that the sample contains one or more CAR-responsive steroids and/or xenochemicals, such as estrogen or PB.

These and additional features are further explained by the following non-limiting examples.

EXAMPLE 1

Hormone Responsiveness of mCAR is Associated with the Ligand Binding Domain (LBD)

To determine the structural basis of the hormone responsiveness observed in the mouse CAR (mCAR), chimeric mouse and human CARs were constructed, and their response to steroid hormones measured in cell-based transfection assay.

Employing multiple sequence alignments (Giguere, *Endocr Rev* 20:689-725, 1999), the putative DNA and ligand binding domains (DBD and LBD, respectively) and the hinge region were defined for mouse and human CAR (mCAR and hCAR) amino acid sequences (FIG. 1). From this analysis, cDNAs encoding various chimeric receptors were constructed between mCAR and hCAR at junctions of the domain and hinge regions, and cloned into pCR3 as follows.

mCAR and hCAR expression vectors were constructed by cloning an entire mCAR (GenBank Accession No: AF009327, deposited on Jul. 22, 1997; SEQ ID NO: 15) or hCAR (GenBank Accession No: Z30425, deposited on Mar. 8, 1994; SEQ ID NO: 17) coding sequence into BamHI and XhoI sites of pCR3 plasmid as described previously (Sueyoshi et al., *J Biol Chem* 274:6043-6, 1999). Polymerase chain reaction (PCR) was used to amplify the desired hCAR or mCAR fragment from the plasmid. The amplified fragments used for the chimeras were nucleotides encoding amino acids: 1 to 86 of mCAR and 77 to 348 of hCAR (mhh), 1 to 116 of mCAR and 107 to 348 of hCAR (mmh), 1 to 76 of hCAR and 87 to 358 of mCAR (hmm), 1 to 106 of hCAR and 117 to 358 of mCAR (hhm). These fragments were PCR amplified using pfu polymerase and enzymatically phosphorylated primers. The amplified fragments were ligated, and a second PCR amplification was performed on the ligated DNA with the primers for 5' and 3' end of the chimeric DNA. The resulting second PCR products were cloned into a pCR3 vector (Invitrogen) with newly created BamHI and XhoI sites at the 5' and the 3' ends, respectively. All chimeras were confirmed by sequencing.

The function of chimeric receptors with respect to their response to steroid hormones was examined by co-transfecting the chimeric receptors with the reporter plasmid $(NR1)_5$-tk (thymidine kinase)-luciferase (Kawamoto et al., *Mol Cell Biol* 19:6318-22, 1999) into HepG2 cells as follows. HepG2 cells (ATCC, Manassas, Va.) were cultured in minimal essential medium supplemented with 10% fetal bovine serum. Cells were plated in 24-well plates one day before transfection. The $(NR1)_5$-tk-luciferase plasmid (0.1 µg) was co-transfected with a CAR expression plasmid described above (0.2 µg) and pRL-SV40 (0.2 µg) (used as the control expression, Promega) into HepG2 cells by calcium phosphate co-precipitation using a CellPhect Transfection kit (Amersham Pharmacia Biotech, Piscataway, N.J.). Sixteen hours later, the transfected cells were treated for another 24 hours with DMSO (as a control), KN62 (Calbiochem), progesterone (Sigma) TCPOBOP (1,4-bis [2-(3,5-dichloropyridyloxy)]benzene) (synthesized using the method described in *Mol. Pharmacol.* 28:445-53, 1985), PB (phenobarbital), and/or E2 (estradiol) (Sigma), and luciferase activity measured using the Dual-Luciferase reporter assay system (Promega, Madison, Wis.). If CAR is constitutively active or activated by one of the agents listed above, if will activate expression of the luciferase gene encoded by the $(NR1)_5$-tk-luciferase plasmid, the production of which can be monitored using a reporter assay.

mCAR activity was repressed by progesterone and re-activated by E2, whereas these steroids did not alter the activity of hCAR. The hormone-responsive repression and activation of mCAR decreased or was absent only when the LBD was replaced with its human counterpart (mhh and mmh). Consistent with the role of mLBD in the hormone responsiveness, hCAR acquired this responsiveness by replacing its LBD with mLBD (hmm and hhm). Thus, the hormone response activity is associated with the mouse LBD.

EXAMPLE 2

Thr350 is a Primary Determinant Conferring Hormone Responsiveness to mCAR

To identify the region of the mouse LBD responsible for the observed hormone responsiveness, chimeric receptors within the mouse LBD were constructed by replacing mouse LBD sequences with corresponding sequences from a human LBD as follows: 1 to 159 of mCAR and 150 to 348 of hCAR (mh159), 1 to 224 of mCAR and 215 to 348 of hCAR (mh224), 1 to 315 of mCAR and 306 to 348 of hCAR (mh315), and 1 to 345 of mCAR and 336 to 348 of hCAR (mh345) (FIG. 1A). These constructs were generated using PCR and standard cloning methods, as described above in EXAMPLE 1. The hormone responsiveness for each construct was examined using the transfection and luciferase assay methods described in EXAMPLE 1.

None of these chimeric receptors was repressed by progesterone, indicating that one or more residues after position 345 in mCAR is responsible for the observed hormone responsiveness. Based on a sequence alignment analysis, the 13 C-terminal residues (positions 346 to 358 of mCAR) constitute an activation function 2 (AF2) domain.

The AF2 domain is a C-terminal sequence of nuclear steroid receptors that modulates a trans-activation function of the receptors. Although it is known that mCAR looses its constitutive activity by an AF2 mutation (Leu352Ala or Glu355Ala) or the deletion of the AF2 domain (Choi et al., *J. Biol Chem* 272:23565-71, 1997), Leu352 and Glu355 are conserved in both mCAR and hCAR and are therefore not likely to determine species differences in the capability of responding to steroid hormones.

Alignment of the C-terminal mCAR 13 residues with the corresponding residues of hCAR (positions 336 to 348) revealed two amino acid differences: Thr350 and Gly354 of mCAR were substituted in hCAR with Met340 and Gln344, respectively. Accordingly, Thr350 and Gly354 of mCAR were mutated to methionine (mCAR$_{T350M}$) and glutamine (mCAR$_{G354Q}$), respectively. In addition, mCAR mutants containing both substitutions (T350M and G354Q, d, were generated). As a control, hCAR Met340 was mutated to Thr (M340T). Mutations were introduced by PCR using the appropriate nucleotide primers (Table 1), and the Quick-Change site-directed mutagenesis system (Stratagene, La Jolla, Calif.) according to the instruction manual. All mutations were confirmed by sequencing. The resulting mutated sequences were cloned into pCR3 vectors and co-transfected into HepG2 cells along with (NR1)$_5$-tk-luciferase plasmid and pRL-SV40. The transfected cells were then treated, and luciferase assays performed as described in EXAMPLE 1.

The mutant mCAR$_{T350M}$ lost its ability to be repressed by progesterone, whereas the mCAR$_{G354Q}$ mutant retained a reduced ability to be repressed by progesterone. The double mutation (mCAR$_{T350M/G354Q}$) showed similar activity as observed with the Thr350 mutant (mCAR$_{T350M}$). In addition to progesterone, testosterone repressed wild-type mCAR but not the T350M mutant. Substituting Met340 with Thr (hCAR$_{M340T}$) did not alter the non-responsiveness of the human receptor activity to steroid hormone.

In dose-dependent experiments, 0.1, 0.3, 1.0, 3.0, or 10 μM of progesterone or 10 μM progesterone with 0.1, 0.3, 1, 3, or 10 μM estradiol was incubated with the transfected cells and luciferase activity determined as described above. Low concentrations of progesterone (1-10 μM) was sufficient to repress NR1-luciferase reporter gene activity of wild-type mCAR, while the mutant mCAR$_{T350M}$ was not repressed at even 10 μM progesterone. In addition, estradiol (E2) fully activated wild-type mCAR in the presence of progesterone (10 μM), whereas mutant mCAR$_{T350M}$ could not be activated by E2. These results indicate that Thr350 is a primary determinant conferring hormone responsiveness to mCAR.

EXAMPLE 3

Thr350 is not Involved in Co-Activation of CAR by SRC-1

AF2 domains regulate receptor activity by direct interaction with co-regulators (Glass and Rosenfeld, *Genes Dev* 14:121-41, 2000). The co-activator steroid receptor co-activator 1 (SRC-1) was previously shown to enhance the CAR-mediated activity of the PB-responsive enhancer module (PBREM) in a cell-based transfection assay (Muang-moonchai et al., *Biochem J* 355:71-8, 2001 and Zelko et al., *Mol Cell Biol* 21:2838-46, 2001). Because Thr350 resides within or near a predicted AF2 domain of mCAR, the role of Thr350 in regulating co-activation was examined by co-transfection of a SRC-1-expression plasmid as follows.

A mouse SRC-1 cDNA corresponding to amino acid residues 633 to 1450 of SRC-1 (GenBank Accession No:

TABLE 1

Primers used to mutate CAR

| Primer description | Primer Sequence | SEQ ID NO. |
|---|---|---|
| T176V mCAR, Forward | TTT GCA GAT ATC AAC GTG TTT ATG GTG CAA CAG | 1 |
| T176V mCAR, Reverse | CTG TTG CAC CAT AAA CAC GTT GAT ATC TGC AAA | 2 |
| T176L mCAR, Forward | TTT GCA GAT ATC AAC CTG TTT ATG GTG CAA GAG | 3 |
| T176L mCAR, Reverse | CTG TTG CAC CAT AAA CAG GTT GAT ATC TGC AAA | 4 |
| L352A mCAR, Forward | TCT GCT ATG ACG CCG GCG CTC GGG GAG ATT TGC | 5 |
| L352A mCAR, Reverse | GCA AAT CTC CCC TAT CGC CGG CGT CAT AGC AGA | 6 |
| M340T/hGAR, forward | CTG TCT GCC ATG ACG CCG CTG CTC CAG GAG | 7 |
| M340T/hCAR, reverse | CTC CTG GAG CAG CGG CGT CAT GGC AGA CAG | 8 |
| T350M/mGAR, Forward | GAA CTG TCT GCT ATG ATG CCG CTG CTC GGG GAG | 9 |
| T350M/mGAR, Reverse | CTC CCC GAG CAG CGG CAT CAT AGC AGA CAG TTC | 10 |
| G354Q/mGAR, Forward | ATG ACG CCG CTG CTC CAG GAG ATT TGC AGT TGA | 11 |
| G354Q/mCAR, Reverse | TCA ACT GCA AAT CTC CTG GAG CAG CGG CGT CAT | 12 |
| T350M/G354Q/mCAR, mh345 mCAR, Reverse | TTC CTC CAA GCG CTG AAG TT | 13 |
| hCAR, Forward | CTG TCT GCC ATG ATG CCG CT | 14 |

U64828), was amplified and cloned into the EcoRI and Hind III site of pcDNA3.1/myc-His(−)B plasmid (Invitrogen), thereby generating the SRC-1-expression plasmid pcDNA3.1-SRC-1. Wild-type mCAR or mCAR$_{T350M}$ was co-transfected with or without the SRC-1-expression plasmid (0.1 µg) into HepG2 cells. The cells were incubated in various concentrations of progesterone (0.1, 0.3, 1, 3, and 10 µM and NR1-luciferase reporter gene activity measured as described in EXAMPLE 1.

Co-expression of SRC-1 increased the trans-activation activity of both wild-type mCAR and mutant mCAR$_{T350M}$ by about 3- to 4-fold (relative to DMSO-treated cells). Even 10 µM progesterone did not repress the SRC-1-dependent increased activity of the mutant receptor. In contrast, SRC-1 prevented the repression of the wild-type mCAR by progesterone at any concentration up to 10 µM. These results indicate that Thr350 does not play a role in the co-activation by SRC-1 in the absence of progesterone under the experimental conditions used. However, Thr350 does regulate the co-activation in the presence of progesterone.

EXAMPLE 4

Thr350 is not Involved in Repression of CAR by KN-62

In addition to the endogenous steroid hormones progesterone and testosterone, the exogenous Ca$^{2+}$/calmodulin kinase inhibitor, KN-62 represses the constitutive activity of mCAR, but not hCAR (Kawamoto et al., *Mol Endocrinol* 14:1897-905, 2000). To determine if Thr350 is involved in mCAR repression by KN-62 as observed with steroid hormones, the domain-based chimeric receptors generated in EXAMPLE 1 were used to localize a region of mRNA responsible for repression by KN-62. Experiments were performed as described in EXAMPLE 1, except that KN-62 was used instead of progesterone.

KN-62 repressed the activity of chimeras hmm and hhm and the repressed chimeric receptors by 2-4 fold, and were re-activated by TCPOBOP. These results indicate that the mouse LBD dictates the KN-62 repression of mCAR as well as the re-activation by TCPOBOP.

To determine if this effect could be disrupted by mutating Thr350 to a Met, the mCAR$_{T350M}$ mutant described in EXAMPLE 2 was used. The KN-62 repression was examined with and without the co-expression of SRC-1 (EXAMPLE 3). HepG2 cells were co-transfected, treated, and luciferase assays performed as described in EXAMPLES 1-3, except that KN-62 at various concentrations (0.1, 0.3, 1, 3, and 10 µM) was used instead of progesterone. KN-62 similarly repressed the activities of wild-type mCAR and mutant mCAR$_{T350M}$, indicating that the repression by KN-62 did not depend on Thr at position 350 in mCAR. Therefore, the structural basis for the hormonal repression differs from that by xenochemicals such as KN-62.

The degree of the repression was influenced by co-expression of SRC-1: 80% and only 20-30% repression in the presence and absence of SRC-1, respectively. However, the repression was not affected by the mutation of Thr350. Thr350 does not appear to play a role either in the co-regulation by SRC-1 or in the repression by KN-62. This is in contrast to the role of Thr350 in the repression by steroid hormones described in EXAMPLE 2.

The presence of a T350M mutation, for example in a cell or in an organism, can have a dominant-negative effect on wild type CAR and thus suppresses hormone responsiveness.

EXAMPLE 5

Three-Dimensional Modeling of mCAR

The results discussed in EXAMPLE 2 demonstrate that the residue at position 350 is sufficient to specify the steroid hormone responsiveness of mCAR, despite the fact that the receptor can be promiscuously activated by numerous endogenous and foreign chemicals that are structurally unrelated. This paradoxical characteristic of the receptor function is reminiscent of the drug/steroid-metabolizing enzymes such as cytochrome P450. Considering the large number of genes that are collectively regulated by the nuclear orphan receptors in response to diverse chemicals, finding the structural principles governing the paradox can be used to predict pharmacological and toxicological effects of a given chemical.

As disclosed in the examples above, mutating Thr at position 350 of mCAR to the corresponding Met in hCAR abolishes the repression of mCAR by progesterone and testosterone. Based on the X-ray crystal structure of pregnane X receptor (PXR) (another nuclear orphan receptor) (Redinbo et al., *Science* 292:2329-33, 2001), a three-dimensional (3D) structure of mCAR was generated using the program "O" (Zou et al. *Acta Crystallogr. Sect. A* 47:110-9, 1991). As shown in FIGS. 2A and 2B, the 3D model of mCAR reveals side-chain (hydrogen bond) interaction between Thr350 and Thr176. The corresponding spatial positions in hCAR are Met340 and Thr166.

EXAMPLE 6

Mutation Analysis of mCAR Thr176 mCAR Thr176 was mutated to various amino acids using the PCR mutagenesis methods described in EXAMPLE 2. One skilled in the art will understand that analogous mutations can be made in any CAR sequence obtained from another organism, such as hCAR T166, and the resulting peptide used as described herein.

The resulting mutants (0.2 µg) were co-transfected into HepG2 cells along with the (NR1)$_5$-tk-luciferase plasmid (0.1 µg) and pRL-SV40 (0.2 µg), treated with DMSO, PB, TCPOBOP, chlorpromazine (CPZ), methoxychlor (MTC), 1,1,1-trichloro1,2-bis(o,p'-chlorophenyl)ethane (DDT), or clotrimazole (CTZ), and subjected to a luciferase reporter gene activation assay using a PB-responsive enhancer module (PBREM) as described in EXAMPLE 1.

A single mutation of Thr176 to valine (T176V) or to leucine (T176L) decreased the constitutive activity of mCAR. In addition, TCPOBOP effectively activated mutated mCAR. This activation did not require exogenous SRC-1, although activity increased as exogenous SRC-1 increased.

EXAMPLE 7

Mutation Analysis of mCAR Leu 352 and hCAR Leu 342/343

To examine the role of Leu352 in mCAR activity, site-directed mutagenesis was used as described in EXAMPLES 2 and 6. One skilled in the art will understand that a corresponding mutation can be made in hCAR (i.e. hCAR Leu342), and the resulting peptide used as described herein.

The resulting mutants were co-transfected into HepG2 cells, treated with DMSO, PB, TCPOBOP, CPZ, or E2 and subjected to a luciferase reporter gene activation assay using a PB-responsive enhancer module (PBREM) as described in EXAMPLES 1-3.

An Ala substitution of Leu352 (L352A) of mCAR decreased mCAR constitutive activity, as was observed in the T176V mutant (EXAMPLE 6). In addition, the L352A mutant was activated by TCPOBOP, as well as estradiol and chloropromazine, but only in the presence of exogenous SRC-1.

To decrease the constitutive activity of hCAR, corresponding mutations were made in a human CAR sequence using site-directed mutagenesis as described in EXAMPLES 2 and 6. An Ala substitution of Leu342 (L342A) of hCAR, as well as the double mutation (L342A/L343A) decreased hCAR constitutive activity, as was observed for the corresponding mCAR mutant.

In summary, mCAR Thr176 and Leu352 and hCAR Leu342 and Leu 343 provide CAR with structural constraint to maintaining the constitutive activity. The mutations decrease or abrogate the constitutive activity of CAR, while retaining the capability of being activated by agonistic chemicals. These residues can play roles in constraining structure of the receptor favor for its constitutive binding to co-regulators such as SRC-1 in cell-based transfection assay.

EXAMPLE 8

Methods of Screening Test Agents

Methods are disclosed for screening test agents to identify agents that include xenochemical and/or steroid metabolizing activity. Such agents increase transcription of a nucleic acid sequence, such as a drug metabolizing enzyme, operably linked to an enhancer element. In particular examples, transcription is increased by at least 10%, at least 20%, at least 50%, at least 75%, at least 100%, at least 200% or even greater, as compared to transcription levels in the absence of the agent Screening of potential agents that increase such transcription is facilitated by the disclosure herein of non-CAR polypeptides that have decreased constitutive activity in vitro, for example a decrease of at least 20%, at least 50%, at least 75%, at least 80%, at least 90%, at least 95%, at least 98%, using the cell based transfection assay described in EXAMPLE 1. For example, agents can be screened for their ability to increase transcription of a drug-metabolizing enzyme, such as a steroid and/or xenochemical metabolizing enzyme.

Synthetic drug databases (which can be licensed from drug companies) can be screened to identify drugs that increase transcription of a nucleic acid sequence operably linked to an enhancer element, herein such drugs can include steroid and/or xenochemical metabolizing activity. For example, a non-CAR peptide and one or more enhancer elements operably linked to a reporter gene which produces a detectable product are in a cell, such as a transgenic cell, and the cell is exposed to the test agent. If the product is detected following contact with the cell, this indicates that the test agent conferred the ability of non-CAR to increase transcription of a nucleic acid sequence operably linked to an enhancer element, thereby resulting in production of the product from the reporter gene. If no product is detected following contact with the cell, this indicates that the test agent did not confer the ability of non-CAR to increase transcription of a nucleic acid sequence operably linked to an enhancer element.

The enhancer element used is chosen based on the type of agent one wants to identify. For example, if the identification of an agent that activates genes that metabolize PB or PB-type compounds is desired, then enhancer elements that include a PB enhancer are used, such as NR1 or PBREM. Alternatively, if the identification of an agent that activates genes that metabolize steroid compounds is desired, then enhancer elements that include a steroid enhancer are used. Other examples of drug/enhancer combinations that can be tested include, but are not limited to: ER6 and XREM of CYP3A genes, gtPBREM of UDP-glucuronosyltransferase, and the peroxisome proliferator response element of the enoyl-CoA hydratase/3-hydroxyacyl-CoA dehydrogenase.

Alternatively, cells expressing a non-CAR peptide, such as in a transgenic animal, are administered one or more test agents. Subsequently, expression of non-CAR regulated genes is determined, for example as described in Ueda et al. (Mol. Pharmcol. 61:1-6,2002, herein incorporated by reference). Examples of non-CAR regulated genes include, but are not limited to CYP2B10, CYP3A11, and amino levulinate synthase 1. Briefly, RNA is obtained from the animal or cells following administration of the test agent(s). In one example, animals are sacrificed and total liver RNA obtained using TRIzol reagent (Invitrogen, Carlsbad, Calif.) and enrichment for mRNA can be achieved by using Oligotex mRNA kit (QIAGEN, Valencia, Calif.) according to the manufacturers' instructions. cDNA is prepared from the RNA using standard molecular biology techniques. The cDNA can be used as a template for RT-PCR to amplify one or more genes of interest, using the appropriate primers. Alternatively or in addition, microarray methods can be used to analyze the mRNA samples. For example, mRNA obtained from the exposed cells is labeled, for example with Cy3 and Cy5-conjugated dUTP using reverse transcription, and the resulting product hybridized to a cDNA microarray chip (containing cDNA from the same organism as the cell or animal). Following hybridization, the array is scanned and images analyzed for fluorescence intensity.

Test agents such as synthetic drugs or peptides that are observed to increase transcription of a nucleic acid sequence operably linked to an enhancer element, are good candidates for therapies, such as treatment of subjects exposed to one or more xenochemicals, or a subject in whom altered levels of one or more steroids is desired.

EXAMPLE 9

Production of Sequence Variants

Disclosed herein are non-CAR sequences, and methods of using non-CAR sequences. It is understood by those skilled in the art that use of alternative non-CAR sequences (such as polymorphisms, fragments, mutants, fusions, or other variants) can be used to practice the screening methods of the present disclosure, as long as the distinctive functional characteristics of the non-CAR antigen are retained. For example, non-CAR variants can be used to practice the methods disclosed herein if such variants retain the characteristic of having decreased constitutive activity in vitro, for example a decrease of at least 20%, at least 50%, at least 75%, at least 80%, at least 90%, at least 95%, or at least 98% of constitutive activity. This activity can readily be determined using the assays disclosed herein, for example the cell-based transfection assay described in EXAMPLE 1. In yet other examples, non-CAR variants can be used to practice methods disclosed herein if they retain their ability to be activated by agonistic compounds, such as xenochemicals and/or steroids, that is, retain their ability to increase transcription of the nucleic acid sequence operably linked to the enhancer element in the presence of one or more, such as two or more, such as 10 or more, xenochemicals and/or steroids.

This disclosure facilitates the use of DNA molecules, and thereby proteins, derived from a native (wild-type) CAR protein but vary in their precise nucleotide or amino acid sequence from the native sequence. Such variants can be obtained through standard molecular biology laboratory techniques and the sequence information disclosed herein. DNA molecules and nucleotide sequences derived from a native DNA molecule can also be defined as DNA sequences that hybridize under stringent conditions to the DNA sequences disclosed, or fragments thereof. Hybridization conditions resulting in particular degrees of stringency vary depending upon the nature of the hybridization method and the composition and length of the hybridizing DNA used. Generally, the temperature of hybridization and the ionic strength (especially the Na$^+$ concentration) of the hybridization buffer determines hybridization stringency. Calculations regarding hybridization conditions required for attaining particular amounts of stringency are discussed by Sambrook et al. (*Molecular Cloning: A Laboratory Manual*, Cold Spring Harbor, N.Y., 1989, Chapters 9 and 11), herein incorporated by reference. Hybridization with a target probe labeled with [$^{32}$P]-dCTP is generally carried out in a solution of high ionic strength such as 6×SSC at a temperature that is about 5-25° C. below the melting temperature, $T_m$. The term $T_m$ is the temperature (under defined ionic strength and pH) at which 50% of the target sequence remains hybridized to a perfectly matched probe or complementary strand. The $T_m$ of such a hybrid molecule may be estimated from the following equation (Bolton and McCarthy, *Proc. Natl. Acad. Sci. USA* 48:1390, 1962): $T_m=81.5°$ C.$-16.6(\log_{10}[Na^+])+0.41(\%$ G+C$)-0.63(\%$ formamide$)-(600/I)$; where I=the length of the hybrid in base pairs.

The degeneracy of the genetic code further widens the scope of the present disclosure as it enables variations in the nucleotide sequence of a non-CAR DNA molecule while maintaining the amino acid sequence of the encoded non-CAR protein. For example, the amino acid Ala is encoded by the nucleotide codon triplet GCT, GCG, GCC and GCA. Thus, the nucleotide sequence can be changed without affecting the amino acid composition of the encoded protein or the characteristics of the protein. Based upon the degeneracy of the genetic code, variant DNA molecules can be derived from a cDNA molecule using standard DNA mutagenesis techniques as described above, or by synthesis of DNA sequences. DNA sequences that do not hybridize under stringent conditions to the cDNA sequences disclosed by virtue of sequence variation based on the degeneracy of the genetic code are also comprehended by this disclosure.

Non-CAR variants, fragments, mutants, variants, fusions, and polymorphisms retain the characteristic of having decreased constitutive activity in vitro, as determined using the assays disclosed he, for example a cell-based transfection assay (EXAMPLE 1). Variants and fragments of a protein retain at least 70%, 80%, 85%, 90%, 95%, 98%, or greater sequence identity to a protein amino acid sequence and maintain the functional activity of the protein as understood by those in skilled in the art.

Amino acid substitutions are typically of single residues; for example 1, 2, 3, 4, 5, 10 or more substitutions; insertions usually will be from about 1 to 10 amino acid residues; and deletions can range about from 1 to 30 residues. Substitutions, deletions, insertions or any combination thereof can be combined to arrive at a final construct Ideally, mutations in the DNA encoding the protein should not place the sequence out of reading frame and will not create complementary regions that could produce secondary mRNA structure. The simplest modifications involve the substitution of one or more amino acid residues (for example 2, 5 or 10 residues) for amino acid residues having conservative substitutions.

Such variants can be readily selected for additional testing by performing an assay (such as those described in EXAMPLES 1-7) to determine if the non-CAR variant retains the characteristic of having decreased constitutive activity in vitro.

EXAMPLE 10

Recombinant Expression

With publicly available CAR cDNA and amino acid sequences (for example see Genbank Accession Nos. AF009327 and Z30425), and the disclosure herein of mutations that result in a non-CAR sequence, additional non-CAR sequences can be generated that vary from those disclosed. Expression and purification by standard laboratory techniques of any variant, such as a polymorphism, mutant, fragment or fusion of the disclosed non-CAR sequences is enabled. One skilled in the art will understand that non-CAR and fragments thereof can be produced recombinantly in any cell or organism of interest, and purified prior to use, for example prior to immunization of a subject to produce antibodies, or prior to screening test agents.

Methods for producing recombinant proteins are well known in the art. Therefore, the scope of this disclosure includes recombinant expression of any non-CAR protein or fragment thereof. For example, see U.S. Pat. No. 5,342,764 to Johnson et al.; U.S. Pat. No. 5,846,819 to Pausch et al.; U.S. Pat. No. 5,876,969 to Fleer et al. and Sambrook et al. (*Molecular Cloning: A Laboratory Manual*, Cold Spring Harbor, N.Y., 1989, Ch. 17, herein incorporated by reference).

Briefly, partial, full-length, or variant non-CAR cDNA sequences, that encode for a non-CAR protein or peptide, can be ligated into an expression vector, such as a bacterial expression vector. Proteins and/or peptides can be produced by placing a promoter upstream of the cDNA sequence. Examples of promoters include, but are not limited to lac, trp, tac, trc, major operator and promoter regions of phage lambda, the control region of fd coat protein, the early and late promoters of SV40, promoters derived from polyoma, adenovirus, retrovirus, baculovirus and simian virus, the promoter for 3-phosphoglycerate kinase, the promoters of yeast acid phosphatase, the promoter of the yeast alpha-mating factors and combinations thereof.

Vectors suitable for the production of intact native proteins include pKC30 (Shimatake and Rosenberg, 1981, *Nature* 292:128), pKK177-3 (Amann and Brosius, 1985, *Gene* 40:183) and pET-3 (Studiar and Moffatt, 1986, *J. Mol. Biol.* 189:113). A DNA sequence can be transferred to other cloning vehicles, such as other plasmids, bacteriophages, cosmids, animal viruses and yeast artificial chromosomes (YACs) (Burke et al., 1987, *Science* 236:806-12). These vectors can be introduced into a variety of hosts including somatic cells, and simple or complex organisms, such as bacteria, fungi (Timberlake and Marshall, 1989, *Science* 244:1313-7), invertebrates, plants (Gasser and Fraley, 1989, *Science* 244:1293), and mammals (Pursel et al., 1989, *Science* 244:1281-8), that are rendered transgenic by the introduction of the heterologous non-CAR cDNA.

For expression in mammalian cells, a non-CAR cDNA sequence can be ligated to heterologous promoters, such as the simian virus SV40, promoter in the pSV2 vector (Mulligan and Berg, 1981, *Proc. Natl. Acad. Sci. USA* 78:2072-6), and introduced into cells, such as monkey COS-1-cells (Gluzman, 1981, *Cell* 23:175-82), to achieve transient or long-term expression. The stable integration of the chimeric gene construct may be maintained in mammalian cells by biochemical selection, such as neomycin (Southern and Berg, 1982, *J. Mol. Appl. Genet.* 1:327-41) and mycophoenolic acid (Mulligan and Berg, 1981, *Proc. Natl. Acad. Sci. USA* 78:2072-6).

The transfer of DNA into eukaryotic, such as human or other mammalian cells, is a conventional technique. The vectors are introduced into the recipient cells as pure DNA (transfection) by, for example, precipitation with calcium phosphate (Graham and vander Eb, 1973, *Virology* 52:466) strontium phosphate (Brash et al., 1987, *Mol. Cell Biol.* 7:2013), electroporation (Neumann et al., 1982, *EMBO J.* 1:841), lipofection (Felgner et al., 1987, *Proc. Natl. Acad. Sci USA* 84:7413), DEAE dextran (McCuthan et al., 1968, *J. Natl. Cancer Inst.* 41:351), microinjection (Mueller et al., 1978, *Cell* 15:579), protoplast fusion (Schafner, 1980, *Proc. Natl. Acad. Sci. USA* 77:2163-7), or pellet guns (Klein et al., 1987, *Nature* 327:70). Alternatively, the cDNA can be introduced by infection with virus vectors, for example retroviruses (Bernstein et al., 1985, *Gen. Engrg.* 7:235) such as adenoviruses (Ahmad et al., 1986, *J. Virol.* 57:267) or Herpes (Spaete et al., 1982, *Cell* 30:295).

EXAMPLE 11

Methods for In Vivo or Ex Vivo Non-CAR Expression

The present disclosure provides methods of expressing non-CAR, or a functional equivalent thereof, in a cell or tissue in vivo. Such methods are useful if non-constitutive CAR activity desired, such as for repression of an endogenous CAR, since non-CAR can act as a dominant negative receptor.

In one example, transfection of the cell or tissue occurs in vitro. In this example, the cell or tissue is removed from a subject and then transfected with an expression vector containing the desired cDNA. The transfected cells produce functional protein and can be reintroduced into the subject. In another example, a nucleic acid is administered to the subject directly, and transfection occurs in vivo.

The scientific and medical procedures required for human cell transfection are now routine. The public availability of CAR cDNAs, as well as the disclosure herein of the role of mutations that result in a non-CAR sequence that has decreased constitutive activity in vitro, allows the development of human (and other mammals) in vivo gene expression based upon these procedures. Immunotherapy of melanoma patients using genetically engineered tumor-infiltrating lymphocytes (TILs) has been reported by Rosenberg et al. (*N. Engl. J. Med.* 323:570-8, 1990), wherein a retrovirus vector was used to introduce a gene for neomycin resistance into TILs. A similar approach can be used to introduce a non-CAR cDNA into subjects.

In some examples, a method of treating subjects in which less CAR expression is desired, is disclosed. These methods can be accomplished by introducing a gene coding for non-CAR into a subject. A general strategy for transferring genes into donor cells is disclosed in U.S. Pat. No. 5,529,774, incorporated by reference. Generally, a gene encoding a protein having therapeutically desired effects is cloned into a viral expression vector, and that vector is then introduced into the target organism. The virus infects the cells, and produces the protein sequence in vivo, where it has its desired therapeutic effect. Zabner et al. (*Cell* 75:207-16, 1993). It may only be necessary to introduce the genetic or protein elements into certain cells or tissues. However, in some instances, it may be more therapeutically effective and simple to treat all of a subject's cells, or more broadly disseminate the vector, for example by intravascular administration.

The nucleic acid sequence encoding non-CAR is under the control of a suitable promoter. Suitable promoters that can be employed include, but are not limited to, the gene's native promoter, retroviral LTR promoter, or adenoviral promoters, such as the adenoviral major late promoter; the CMV promoter; the RSV promoter; inducible promoters, such as the MMTV promoter; the metallothionein promoter; heat shock promoters; the albumin promoter; the histone promoter; the α-actin promoter; TK promoters; B19 parvovirus promoters; and the ApoAI promoter. However the scope of the disclosure is not limited to specific promoters.

The recombinant nucleic acid can be administered to the subject by any method that allows the recombinant nucleic acid to reach the appropriate cells. These methods include injection, infusion, deposition, implantation, or topical administration. Injections can be intradermal or subcutaneous. The recombinant nucleic acid can be delivered as part of a viral vector, such as avipox viruses, recombinant vaccinia virus, replication-deficient adenovirus strains or poliovirus, or as a non-infectious form such as naked DNA or liposome encapsulated DNA, as further described in EXAMPLE 12.

EXAMPLE 12

Viral Vectors for In Vivo Gene Expression

Viral vectors can be used to express a desired non-CAR sequence in vivo. Methods for using such vectors for in vivo gene expression are well known in the art (for example see U.S. Pat. No. 6,306,652 to Fallaux et al., U.S. Pat. No. 6,204,060 to Mehtali et al., U.S. Pat. No. 6,287,557 to Boursnell et al, and U.S. Pat. No. 6,217,860 to Woo et al., all herein incorporated by reference). Specific examples of such vectors include, but are not limited to: adenoviral vectors; adeno-associated viruses (AAV); retroviral vectors such as MMLV, spleen necrosis virus, RSV, Harvey Sarcoma Virus, avian leukosis virus, HIV, myeloproliferative sarcoma virus, and mammary tumor virus, as well as and vectors derived from these viruses. Other viral transfection systems may also be utilized, including Vaccinia virus (Moss et al, 1987, *Annu. Rev. Immunol.* 5:305-24), Bovine Papilloma virus (Rasmussen et al, 1987, *Methods Enzymol.* 139:642-54), and herpes viruses, such as Epstein-Barr virus (Margolskee et al., 1988, *Mol. Cell. Biol.* 8:2837-47). In another example, RNA-DNA hybrid oligonucleotides, as described by Cole-Strauss et al (*Science* 273:1386-9, 1996) are used.

Viral particles are administered in an amount effective to produce a therapeutic effect in a subject. The exact dosage of viral particles to be administered is dependent upon a variety of factors, including the age, weight, and sex of the subject to be treated, and the nature and extent of the disease or disorder to be treated. The viral particles may be administered as part of a preparation having a titer of viral particles of at least $1 \times 10^{10}$ pfu/ml, and in general not exceeding $2 \times 10^{11}$ pfu/ml. The viral particles can be administered in combination with a pharmaceutically acceptable carrier in a volume up to 10 ml. The pharmaceutically acceptable carrier may be, for example, a liquid carrier such as a saline solution, protamine sulfate (Elkins-Sinn, Inc., Cherry Hill, N.J.), or Polybrene (Sigma Chemical). Conventional pharmaceutically acceptable carriers are disclosed in *Remington's Pharmaceutical Sciences*, by Martin, Mack Publishing Co., Easton, Pa., 15th Edition, 1975.

EXAMPLE 13

Generation and Expression of Fusion Proteins

Non-CAR fusion proteins or peptides that include a non-CAR sequence (such as full-length non-CAR, or fragments, mutants, variants, or polymorphisms of non-CAR) can be generated using standard methods known to those skilled in the art (for example see U.S. Pat. No. 6,057,133 to Bauer et al. and U.S. Pat. No. 6,072,041 to Davis et al., both incorporated by reference). In one example, linker regions are used to space the two portions of the protein from each other and to provide flexibility between the two peptides, such as a polypeptide of between 1 and 500 amino acids. Other moieties can also be included, such as a binding region (i.e. avidin or an epitope, such as a polyhistadine tag) which can be useful for purification and processing of the fusion protein. In addition, detectable markers can be attached to the fusion protein.

EXAMPLE 14

Transgenic Animals

Animals that express non-CAR, or a variant or fusion thereof that retains non-CAR activity, in their cells are prepared to further demonstrate the role(s) of CAR in gene regulation. For example, transgenic animals, such as mice, that express non-CAR can be used to test or screen for agents that decrease the toxicity of xenochemicals, such as environmental pollutants, by metabolizing such xenochemicals. Such animals have a phenotype that reflects a lack of CAR function.

Methods for generating transgenic mice are described in Gene Targeting, A. L. Joyuner ed., Oxford University Press, 1995 and Watson, J. D. et al., Recombinant DNA 2nd Ed., W.H. Freeman and Co., New York, 1992, Chapter 14 as well as in U.S. Pat. Nos. 5,574,206; 5,723,719; 5,175,383; 5,824,838; 5,811,633; 5,620,881; and 5,767,337, herein incorporated by reference. Briefly, a vector including the desired non-CAR sequence, such as the plasmids and vectors disclosed in EXAMPLES 10-12, is generated. The plasmid is linearized, purified, and microinjected into mouse embryos that are implanted into surrogate mothers. Pups are screened for the presence of the transgene by PCR on tail snippets. Once at least one positive founder male and one positive founder female containing the transgene in their genomes are identified, the founder animals are separately bred into a C57b16 background for several generations until homozygous positive mice are obtained that breed true (generated all positive litters). The phenotypes of the mice, such as their ability to respond to xenochemicals such as therapeutic drugs, synthetic chemicals, and naturally-occurring chemicals can be determined.

EXAMPLE 15

Analysis of Samples

This example describes methods that can be used to detect the presence of one or more CAR-responsive steroids and/or xenochemicals, such as estrogen or estrogen-like compounds, and PB and PB-like compounds, in a sample. The sample can be a biological sample obtained from a subject, for example a subject suspected of being exposed to a CAR-responsive xenochemical. Alternatively, the sample can be an environmental sample, for example a water sample obtained from a river or lake that is suspected of containing one or more CAR-responsive steroids and/or xenochemicals.

Samples containing one or more CAR-responsive steroids and/or xenochemicals will increase transcription of a nucleic acid sequence, such as a drug metabolizing enzyme, operably linked to an appropriate enhancer element in the presence of non-CAR. In particular examples, transcription is increased by at least 10%, at least 20%, at least 50%, at least 75%, at least 100%, at least 200% or even greater, as compared to transcription levels in the absence of the sample.

A cell expressing one or more non-CAR peptides, such as a transgenic cell, is contacted with the sample of interest, and the resulting effect on steroid and/or xenochemical metabolizing activity determined. For example, the cell can express one or more non-CAR peptides as well as a nucleic acid sequence operably linked to an enhancer element Examples of nucleic acid sequences which can be used include, but are not limited to, a drug metabolizing enzyme or a reporter gene sequence. If the sample contains an agent(s) that induces steroid and/or xenochemical metabolizing enzyme(s), non-CAR will be activated and interact with the enhancer element, thereby increasing transcription of the nucleic acid sequence operably linked to the enhancer element. Detection of transcription of the nucleic acid sequence can is used to make a dermination as to whether a CAR-responsive steroid(s) or xenochemical(s) is present in the sample. For example if the nucleic acid sequence encodes for a reporter gene, the gene produces a detectable product, such as luciferase, which can be detected. The presence of the detectable product indicates that the sample contains one or more CAR-responsive steroids and/or xenochemicals, such as estrogen or PB.

If desired, one can use additional methods to identify the particular steroid and/or xenochemical present. However, based on the enhancer element used, one can determine at least the type of steroid and/or xenochemical present. For example, the enhancer element can be chosen based on the agent one wants to identify. For example, if the identification of an agent that activates genes that metabolize PB or PB-type compounds is desired, then enhancer elements that include a PB enhancer are used, such as NR1 or PBREM. Alternatively, if the identification of an agent that activates genes that metabolize steroid compounds is desired, then enhancer elements that include a steroid enhancer are used. Other examples of drug/enhancer combinations that can be used include, but are not limited to: ER6 and XREM of CYP3A genes, gtPBREM of UDP-glucuronosyltransferase, and the peroxisome proliferator response element of the enoyl-CoA hydratase/3-hydroxyacyl-CoA dehydrogenase.

In view of the many possible embodiments to which the principles of our disclosure may be applied, it should be recognized that the illustrated embodiments are only particular examples of the disclosure and should not be taken as a imitation on the scope of the disclosure. Rather, the scope of the disclosure is in accord with the following claims. We therefore claim as our invention all that comes within the scope and spirit of these claims.

We claim:

1. An isolated polypeptide, wherein the amino acid sequence of the polypeptide comprises a human constitutively active nuclear orphan receptor (CAR) polypeptide sequence of SEQ ID NO: 18 comprising one to ten mutations, wherein the one to ten mutations render the isolated polypeptide less constitutively active than the human CAR polypeptide of SEQ ID NO: 18.

2. The isolated polypeptide of claim 1, wherein the mutations comprise mutations at human CAR (hCAR) position Leu342 and hCAR position Leu343 of SEQ ID NO: 18.

3. The isolated polypeptide of claim 1, wherein the one to ten mutations corresponds to mutations at hCAR position Leu342 or hCAR position Leu343 of SEQ ID NO: 18.

4. The isolated polypeptide of claim 3, wherein the one to ten mutations comprise a Leu342 to Ala342 (L342A) mutation or a Leu343 to Ala343 (L343A) mutation.

5. The isolated polypeptide of claim 1, wherein the isolated polypeptide further comprises one to ten conservative amino acid substitutions which do not substantially alter the constitutive activity of the polypeptide.

6. The isolated polypeptide of claim 1, wherein the polypeptide induces xenochemical metabolizing activity of a xenochemical-metabolizing enzyme, and wherein the xenochemical metabolizing activity can be detected in vitro.

7. The isolated polypeptide of claim 6, wherein the xenochemical-metabolizing enzyme metabolizes a xenochemical selected from the group consisting of phenobarbital and 1,4-bis[2-(3,5-dichloropyridyloxy)]benzene (TCPOBOP).

8. The isolated polypeptide of claim 1, wherein the polypeptide induces steroid metabolizing activity of a steroid-metabolizing enzyme, and wherein the steroid metabolizing activity can be detected in vitro.

9. The isolated polypeptide of claim 8, wherein the steroid-metabolizing enzyme metabolizes a steroid selected from the group consisting of estrogen and estradiol.

10. The isolated polypeptide of claim 1, wherein the polypeptide is at least 70% pure.

11. A composition comprising the isolated polypeptide of claim 1 and a pharmaceutically acceptable carrier.

12. An isolated polypeptide, wherein the amino acid sequence of the polypeptide comprises a human constitutively active nuclear orphan receptor (hCAR) polypeptide sequence of SEQ ID NO: 18 comprising one to ten mutations corresponding to mutations at hCAR position Leu342 and/or Leu343, wherein the one to ten mutations render the isolated polypeptide less constitutively active than the hCAR polypeptide of SEQ ID NO: 18.

13. The isolated polypeptide of claim 12 comprising a Leu342 to Ala342 mutation and/or a Leu343 to Ala343 mutation.

* * * * *

```
                         SEQUENCE LISTING

<160> NUMBER OF SEQ ID NOS: 14

<210> SEQ ID NO 1
<211> LENGTH: 33
<212> TYPE: DNA
<213> ORGANISM: Artificial Sequence
<220> FEATURE:
<223> OTHER INFORMATION: Primer

<400> SEQUENCE: 1
tttgcagata tcaacgtgtt tatggtgcaa cag                              33

<210> SEQ ID NO 2
<211> LENGTH: 33
<212> TYPE: DNA
<213> ORGANISM: Artificial Sequence
<220> FEATURE:
<223> OTHER INFORMATION: Primer

<400> SEQUENCE: 2
ctgttgcacc ataaacacgt tgatatctgc aaa                              33

<210> SEQ ID NO 3
<211> LENGTH: 33
<212> TYPE: DNA
<213> ORGANISM: Artificial Sequence
<220> FEATURE:
<223> OTHER INFORMATION: Primer

<400> SEQUENCE: 3
tttgcagata tcaacctgtt tatggtgcaa cag                              33

<210> SEQ ID NO 4
<211> LENGTH: 33
<212> TYPE: DNA
<213> ORGANISM: Artificial Sequence
<220> FEATURE:
<223> OTHER INFORMATION: Primer

<400> SEQUENCE: 4
ctgttgcacc ataaacaggt tgatatctgc aaa                              33

<210> SEQ ID NO 5
<211> LENGTH: 33
<212> TYPE: DNA
<213> ORGANISM: Artificial Sequence
<220> FEATURE:
<223> OTHER INFORMATION: Primer

<400> SEQUENCE: 5
tctgctatga cgccggcgct cggggagatt tgc                              33

<210> SEQ ID NO 6
<211> LENGTH: 33
<212> TYPE: DNA
<213> ORGANISM: Artificial Sequence
<220> FEATURE:
<223> OTHER INFORMATION: Primer

<400> SEQUENCE: 6
gcaaatctcc cctatcgccg gcgtcatagc aga                              33
```

<210> SEQ ID NO 7
<211> LENGTH: 30
<212> TYPE: DNA
<213> ORGANISM: Artificial Sequence
<220> FEATURE:
<223> OTHER INFORMATION: Primer

<400> SEQUENCE: 7
ctgtctgcca tgacgccgct gctccaggag                               30

<210> SEQ ID NO 8
<211> LENGTH: 30
<212> TYPE: DNA
<213> ORGANISM: Artificial Sequence
<220> FEATURE:
<223> OTHER INFORMATION: Primer

<400> SEQUENCE: 8
ctcctggagc agcggcgtca tggcagacag                               30

<210> SEQ ID NO 9
<211> LENGTH: 33
<212> TYPE: DNA
<213> ORGANISM: Artificial Sequence
<220> FEATURE:
<223> OTHER INFORMATION: Primer

<400> SEQUENCE: 9
gaactgtctg ctatgatgcc gctgctcggg gag                           33

<210> SEQ ID NO 10
<211> LENGTH: 33
<212> TYPE: DNA
<213> ORGANISM: Artificial Sequence
<220> FEATURE:
<223> OTHER INFORMATION: Primer

<400> SEQUENCE: 10
ctccccgagc agcggcatca tagcagacag ttc                           33

<210> SEQ ID NO 11
<211> LENGTH: 33
<212> TYPE: DNA
<213> ORGANISM: Artificial Sequence
<220> FEATURE:
<223> OTHER INFORMATION: Primer

<400> SEQUENCE: 11
atgacgccgc tgctccagga gatttgcagt tga                           33

<210> SEQ ID NO 12
<211> LENGTH: 33
<212> TYPE: DNA
<213> ORGANISM: Artificial Sequence
<220> FEATURE:
<223> OTHER INFORMATION: Primer

<400> SEQUENCE: 12
tcaactgcaa atctcctgga gcagcggcgt cat                           33

<210> SEQ ID NO 13
<211> LENGTH: 20
<212> TYPE: DNA
<213> ORGANISM: Artificial Sequence
<220> FEATURE:

```
<223> OTHER INFORMATION: Primer

<400> SEQUENCE: 13
ttcctccaag cgctgaagtt                                                    20

<210> SEQ ID NO 14
<211> LENGTH: 20
<212> TYPE: DNA
<213> ORGANISM: Artificial Sequence
<220> FEATURE:
<223> OTHER INFORMATION: Primer

<400> SEQUENCE: 14
ctgtctgcca tgatgccgct                                                    20
```